(12) United States Patent
Ashok et al.

(10) Patent No.: US 12,274,499 B2
(45) Date of Patent: Apr. 15, 2025

(54) MULTIMODE EYE ANALYZING SYSTEM, METHOD AND COMPUTER-READABLE MEDIUM

(71) Applicant: OPTOS PLC, Dunfermline (GB)

(72) Inventors: Praveen Ashok, Dunfermline (GB); Alan Anderson, Dunfermline (GB)

(73) Assignee: OPTOS PLC, Dunfermline (GB)

(*) Notice: Subject to any disclaimer, the term of this patent is extended or adjusted under 35 U.S.C. 154(b) by 858 days.

(21) Appl. No.: 17/205,501

(22) Filed: Mar. 18, 2021

(65) Prior Publication Data

US 2022/0296094 A1 Sep. 22, 2022

(51) Int. Cl.
*A61B 3/10* (2006.01)
*A61B 3/12* (2006.01)
*A61B 3/14* (2006.01)

(52) U.S. Cl.
CPC ............... *A61B 3/102* (2013.01); *A61B 3/12* (2013.01); *A61B 3/14* (2013.01)

(58) Field of Classification Search
CPC .............. A61B 3/12; A61B 3/14; A61B 3/102
See application file for complete search history.

(56) References Cited

U.S. PATENT DOCUMENTS

| | | | |
|---|---|---|---|
| 5,321,501 A | 1/1994 | Swanson et al. | |
| 6,361,167 B1 | 3/2002 | Su et al. | |
| 7,830,525 B2 | 11/2010 | Buckland et al. | |
| 9,119,563 B2 | 9/2015 | Buckland | |
| 10,849,495 B2 | 12/2020 | Pulaski et al. | |
| 2008/0285043 A1* | 11/2008 | Fercher | G01B 9/02058 356/451 |
| 2011/0299035 A1* | 12/2011 | Suehira | A61B 3/102 356/497 |
| 2013/0141695 A1* | 6/2013 | Buckland | A61B 3/102 359/663 |
| 2020/0107718 A1* | 4/2020 | Pascal | A61B 5/0066 |

(Continued)

OTHER PUBLICATIONS

Sikorski et al. "OCT Biometry (B-OCT): A New Method for Measuring Ocular Axial Dimensions" Journal of Ophthamology, vol. 2109, Article ID 9192456, Aug. 14, 2019 (Year: 2019).*

(Continued)

*Primary Examiner* — Cara E Rakowski
(74) *Attorney, Agent, or Firm* — FAEGRE DRINKER BIDDLE & REATH

(57) ABSTRACT

A multimode optical coherence tomography (OCT) imaging system comprises a light source arranged to emit coherent light in a path to scan a sample. An optical parameter unit is arranged in the path and is operable in at least one selected mode from among a plurality of available operating modes, including at least a first mode, a second mode and a third mode. A detector is arranged to detect reflected light, the reflected light being light reflected in the path as a result of the coherence light scanning the sample. A controller is arranged to control at least one of the light source or the optical parameter unit. The first, second and third modes include a retina mode, anterior segment mode, and biometry mode, respectively. Also provided are a method for operating a multimode OCT imaging system, and a computer-readable storage medium storing a program for performing the method.

31 Claims, 8 Drawing Sheets

(56) References Cited

U.S. PATENT DOCUMENTS

2020/0225021 A1* 7/2020 Wei .................... G01B 9/02027
2022/0095909 A1* 3/2022 Charles .................. A61B 3/102

OTHER PUBLICATIONS

Michelle Cua et al, Retinal Optical Coherence Tomography at 1 μm with dynamic focus control and axial motion tracking, Journal of Biomedical Optics, vol. 21(2), Feb. 2016, pp. 026007-1 to 026007-8.

Josef Bille, High Resolution Imaging in Microscopy and Ophthalmology, New Frontiers in Biomedical Optics, Springer Nature Switzerland AG., 2019, pp. 4-86 (Textbook).

J. Choi et al., "Zoom lens design for a novel imaging spectrometer that controls spatial and spectral resolution individually", Applied Optics, vol. 45, No. 15, May 20, 2006, pp. 3430 to 3441.

Rafael Navarro entitled "The Optical Design of the Human Eye: a Critical Review", Journal of Optometry, vol. 2, Issue 1, pp. 3-18 (2009).

Anterion—Multimode Imaging Platform Optimized for the Anterior Segment (15 sheets), downloaded on Mar. 11, 2021 from https://business-lounge.heidelbergengineering.com/ca/en/products/anterion/anterion/#product-details.

Anterion Brochure—Multimode Imaging Platform Optimized for the Anterior Segment (8 sheets), downloaded on Mar. 11, 2021 from https://business-lounge.heidelbergengineering.com/ca/en/products/anterion/anterion/downloads/#downloads.

Anterion Picture Book—Multimode Imaging Platform Optimized for the Anterior Segment (13 sheets), downloaded on Mar. 11, 2021 from https://business-lounge.heidelbergengineering.com/ca/en/products/anterion/anterion/downloads/#downloads.

Zeiss IOLMaster 700 brochure—Getting fewer refractive surprises (12 sheets), downloaded on Mar. 11, 2021 from https://www.zeiss.com/meditec/int/product-portfolio/optical-biometers/iolmaster-700.html.

Zeiss IOLMaster 700 Total Keratometry compendium (13 sheets), downloaded on Mar. 11, 2021 from https://www.zeiss.com/meditec/int/product-portfolio/optical-biometers/iolmaster-700/specifications.html.

Zeiss IOLMaster 700 webpage—Getting fewer refractive surprises (14 sheets), downloaded on Mar. 11, 2021 from https://www.zeiss.com/meditec/int/product-portfolio/optical-biometers/iolmaster-700.html.

Optopol REVO NX 130 overview webpage (21 sheets)—downloaded on Mar. 11, 2021 from http://www.optopol.com/products/REVO+NX+130.

Optopol REVO NX 130 tech specs webpage (6 sheets)—downloaded on Mar. 11, 2021 from http://www.optopol.com/products/REVO+NX+130.

Optopol REVO NX 130 The Latest OCT Standards brochure (12 sheets)—downloaded on Mar. 11, 2021 from http://www.optopol.com/products/REVO+NX+130.

Zeiss Visante OCT (2 sheets)—downloaded on Mar. 11, 2021 from http://worldeyecare.com/zeiss-visante-oct/.

Introducing SOLIX—Fullrange OCT—Discover What's Next (SOLIX Brochure) (9 sheets)—downloaded on Mar. 11, 2021 from https://www.optovue.com/doc/301-54339_A_Solix-Brochure_WEB-2.pdf.

SOLIX—Ultra High-Speed FULLRange OCT (webpage)—(8 sheets)—downloaded on Mar. 11, 2021 from https://www.optovue.com/international/products/solix.

3D OCT-1 Maestro2, Optical coherence tomography (general)—(4 sheets)—downloaded on Mar. 11, 2021 from https://www.topcon-medical.eu/eu/products/510-3d-oct-1-maestro2-optical-coherence-tomography.html.

* cited by examiner

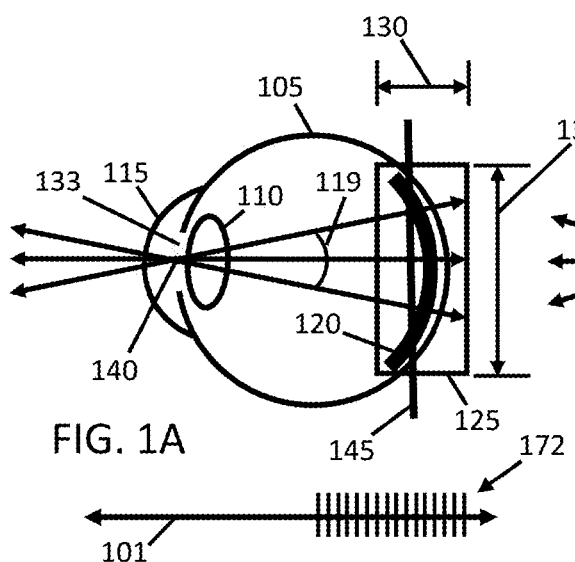
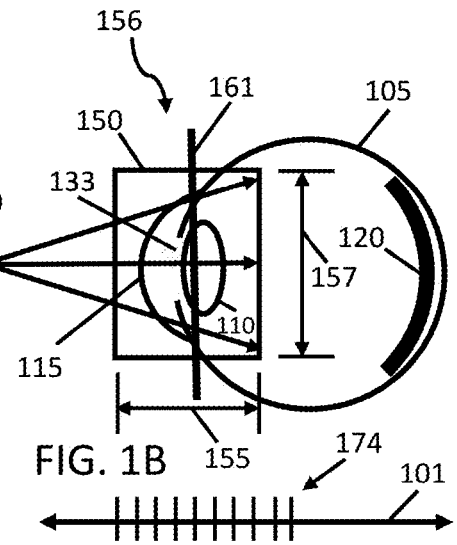
FIG. 1A
FIG. 1B
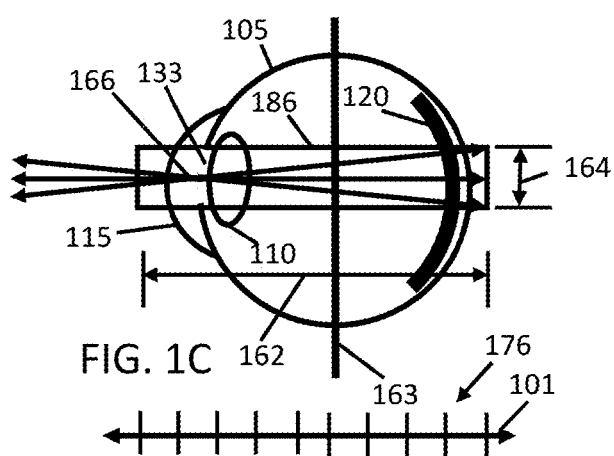
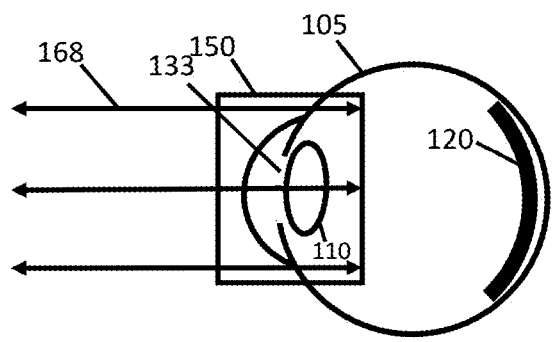
FIG. 1C
FIG. 1D
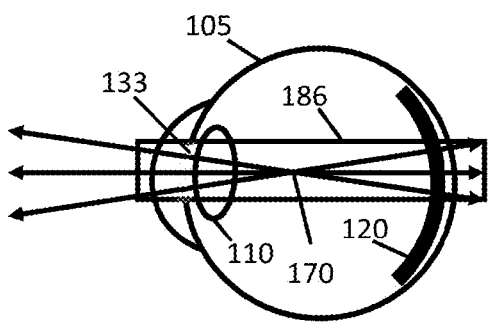
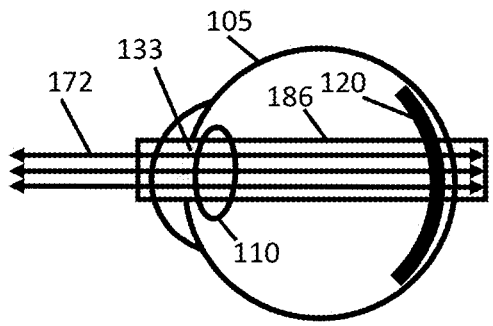
FIG. 1E
FIG. 1F

MULTIMODE EYE ANALYZING SYSTEM, METHOD AND COMPUTER-READABLE MEDIUM

FIELD

Example aspects herein relate to Optical Coherence Tomography (OCT) and, in particular, to systems, methods and computer-readable media for multiple mode eye analysis.

BACKGROUND

Traditionally various separate types of non-invasive eye analysis have been of interest. One type is retina imaging which produces a cross section of the eye's retina located at a back of the eye. The retina has a relatively small thickness compared to the overall dimensions of the eye. The features of interest in the retina for medical diagnosis purposes are similarly relatively small compared to overall dimensions of the eye. A type of non-invasive eye analysis is anterior segment imaging. Anterior segment imaging analyzes the front, or anterior, portion of the eye, including the lens, pupil, cornea, and iris, as well as adjacent regions and structures. These anterior features together comprise a significantly thicker portion of the eye compared to the thickness of the retina. A type of non-invasive eye analysis is imaging and measurement of feature dimensions for use in biometry. For example, an accurate measurement of an axial length of the eye can be useful for determining proper interocular lens power for a prosthetic interocular lens. Axial eye length can be a much larger dimension compared to the thickness of the retina and the thickness of areas of interest for anterior segment imaging.

Typically, known OCT systems have a fixed imaging depth, and involve an imaging depth that is smaller than an axial eye length variability across a patient's eye. For OCT imaging performed by an OCT system, an optical path length of a reference arm of the system typically is matched with an optical path length of a sample arm of the system to enable light from each path to be combined into an interference signal used to derive an image. To account for variability in axial eye length, the path length of the reference or sample arm often is modified using an optical delay line in the reference arm.

Typically, when acquiring OCT measurements of the retina, the optical delay introduced in the reference arm is continually adjusted on a feedback basis in order to place an axial region in which OCT measurements are obtained, across a region of interest in the interior of the eye.

Auto-referencing is a process of achieving matching between a reference arm path length and a sample arm path length. Typically, such matching is achieved by scanning the optical delay line across the axial length range of the patient's eye and identifying a location in the delay line where the optical path length of the reference arm matches that of the sample to be imaged. This matching process typically is iterative in nature and involves capturing data at a given delay line location, checking whether target content is available in the captured data, and moving to another location in the delay line until the target feature is within an imaging depth range of the OCT system. Such a process is time consuming and can take, for example, on the order of a few hundreds of milliseconds to a few seconds to perform. Unfortunately, the longer the process takes, the more likely it is to result in reduced image quality when an image is taken, owing to, for example, undesired patient movements and the like. Known efforts to minimize such degradations include, for example, parallelizing auto-reference routines to patient alignment, but still such efforts involve an iterative process.

SUMMARY

The present inventors have devised, in accordance with a first example aspect herein, a multimode optical coherence tomography (OCT) imaging system comprising a light source arranged to emit coherent light in a path to scan a sample (e.g., an eye), and an optical parameter unit through which the coherence light propagates in the path. The system also comprises a detector arranged to detect reflected light, wherein the reflected light is light that has been reflected in the path as a result of the coherence light scanning the sample by way of the optical parameter unit. The system also comprises a controller arranged to control at least one of the light source or the optical parameter unit such that the multimode OCT system operates in at least one selected mode from among a plurality of available operating modes of the multimode OCT system. The plurality of available operating modes includes at least a first mode, a second mode and a third mode. Each of the plurality of available operating modes provides at least one of a corresponding predetermined axial resolution or a corresponding predetermined imaging depth.

According to one example embodiment herein, the detector comprises a plurality of spectrometers, and each spectrometer detects reflected light within a respective spectral range corresponding to a respective one of the plurality of available operating modes. Also according to an example embodiment herein, the light source comprises a swept source laser and the controller controls the light source by controlling a sweep bandwidth of the swept source laser. In one example embodiment herein, the light source comprises a super-luminescent diode.

In a further example embodiment herein, the controller controls the optical parameter unit by controlling a bandwidth thereof, to thereby control a spectral bandwidth over which reflected light is detected by the detector. At least one of the bandwidth or the spectral bandwidth corresponds to the at least one selected mode.

In accordance with one example aspect herein, the first mode is a retina mode, the second mode is an anterior segment mode, and the third mode is a biometry mode. The corresponding predetermined axial resolution provided by the retina mode is higher than the corresponding predetermined axial resolution provided by the anterior segment mode, and the corresponding predetermined axial resolution provided by the anterior segment mode is higher than the corresponding predetermined axial resolution provided by the biometry mode.

Also according to an example embodiment herein, the controller controls the optical parameter unit to establish at least one of a predetermined focal plane, a predetermined bandwidth, or a scan pivot location, corresponding to the at least one selected mode. In accordance with another example embodiment herein, the optical parameter unit comprises a discrete optical element that is movable along the path. The scan pivot location is in front of, or within, the sample, depending on the at least one selected mode.

In another example embodiment herein, the coherence light scans the sample in a diverging or telecentric manner.

In still another example embodiment herein, the light source emits the coherence light at a frequency that is constant.

Also, in one example embodiment herein, the path is a sample path of the multimode OCT imaging system, and the multimode OCT imaging system also comprises a reference path. The controller is coupled to the detector and obtains an image of the sample based on the reflected light. The image includes a retina image in a case where the at least one selected mode is the retina mode, an anterior segment image in a case where the at least one selected mode is the anterior segment mode, and a biometry image in a case where the at least one selected mode is the biometry mode.

In a further example embodiment herein, the controller also is arranged to perform auto-referencing, wherein the auto-referencing includes detecting a distance between a predetermined feature in the image and another predetermined part of the image, and adjusting a length of the reference path based on the distance. In one example embodiment herein, the auto-referencing further includes, prior to the detecting of the distance, placing the multimode OCT imaging system in a first zoom mode, and, after the adjusting, placing the multimode OCT imaging system in a second zoom mode, wherein the first zoom mode is a zoom out mode and the second zoom mode is a zoom in mode.

The present inventors have also devised, in accordance with another example aspect herein, a method for operating a multimode optical coherence tomography (OCT) imaging system. According to one example embodiment herein, the method comprises selecting at least one mode from among a plurality of available operating modes of the multimode OCT imaging system. The plurality of available operating modes includes at least a first mode, a second mode, and a third mode. The method also comprises operating a light source to emit coherence light in a path towards a sample, and operating an optical parameter unit, arranged in the path between the light source and the sample, to process the light in accordance with the selected at least one mode. Each of the plurality of available operating modes provides at least one of a corresponding predetermined axial resolution or a corresponding predetermined imaging depth. In one example embodiment herein, the first mode is a retina mode, the second mode is an anterior segment mode, and the third mode is a biometry mode.

The method further comprises detecting reflected light by way of a detector, wherein the reflected light is light reflected in the path as a result of the coherence light scanning the sample.

According to one example embodiment herein, the method further comprises controlling at least one of the light source or the optical parameter unit in accordance with the selected at least one mode.

In another example embodiment herein, the detector comprises a plurality of spectrometers. In the detecting, each spectrometer detects reflected light within a respective spectral range corresponding to a respective one of the plurality of available operating modes.

In still another example embodiment herein, the light source comprises a swept source laser, and the operating of the light source includes controlling a sweep bandwidth of the swept source laser in accordance with the selected at least one mode.

In still another example embodiment herein, the operating of the optical parameter unit includes controlling a bandwidth of the optical parameter unit in accordance with the selected at least one mode, to thereby control a spectral bandwidth over which reflected light is detected by the detector.

The path is a sample path of the multimode OCT imaging system, and the multimode OCT imaging system also comprises a reference path. The method can further comprise obtaining an image of the sample based on the reflected light.

In accordance with a further example aspect herein, the method further comprises performing auto-referencing, wherein the auto-referencing includes detecting a distance between a predetermined feature in the image and another predetermined part of the image, and adjusting a length of the reference path based on the distance.

According to an example embodiment herein, the auto-referencing further includes, prior to the detecting of the distance, placing the multimode OCT imaging system in a first zoom mode, and, after the adjusting, placing the multimode OCT imaging system in a second zoom mode. The first zoom mode is a zoom out mode and the second zoom mode is a zoom in mode.

In accordance with still a further example aspect herein, a non-transitory computer readable medium is provided. The medium stores a program that, when executed by a computer processor, causes the computer processor to perform a method for operating a multimode Optical Coherence Tomography (OCT) imaging system. According to an example embodiment herein, the method comprises selecting at least one mode from among a plurality of available operating modes of the multimode OCT imaging system. The plurality of available operating modes includes at least a first mode, a second mode, and a third mode. The method also comprises operating a light source to emit coherence light in a path towards a sample, and operating an optical parameter unit, arranged in the path between the light source and the sample, to process the light in accordance with the selected at least one mode. Each of the plurality of available operating modes provides at least one of a corresponding predetermined axial resolution or a corresponding predetermined imaging depth. The first mode is a retina mode, the second mode is an anterior segment mode, and the third mode is a biometry mode.

BRIEF DESCRIPTION OF DRAWINGS

These and other features, aspects, and advantages of the present invention will become better understood with regard to the following descriptions, claims, and accompanying drawings. It is to be noted, however, that the drawings illustrate only several embodiments of the invention and are therefore not to be considered limiting of the invention's scope as it can admit to other effective embodiments.

FIG. 1A illustrates an example scan for retina imaging.

FIG. 1B illustrates an example diverging scan for anterior segment imaging.

FIG. 1C illustrates an example scan for biometry imaging.

FIG. 1D illustrates an example telecentric scan for anterior segment imaging.

FIG. 1E illustrates an example scan for biometry imaging, involving a diverging pivot after the pupil.

FIG. 1F illustrates an example telecentric scan for biometry imaging.

DETAILED DESCRIPTION

Figure 2A:
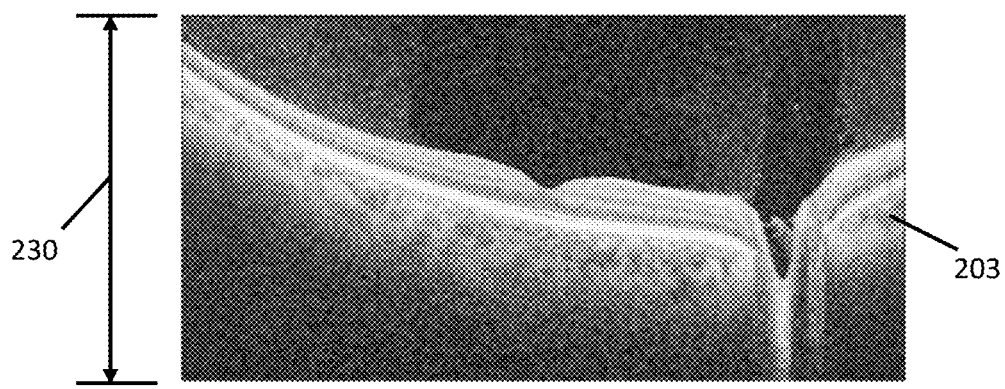
FIG. 2A shows an example retina image obtained in a retinal image mode.

So that the manner in which the features and advantages of embodiments of methods, systems, and computer-readable media of example aspects herein may be understood in more detail, a more particular description of the example aspects briefly summarized above may be had by reference to certain embodiments thereof that are illustrated in the appended drawings, which form a part of this specification. The drawings illustrate only certain example embodiments herein and are, therefore, not to be considered limiting of the scope of the present invention which includes other useful and effective embodiments as well.

Different modes of eye analysis benefit from different optical system characteristics. These characteristics include, by example and without limitation, axial direction, axial resolution, image depth (also referred to herein as "imaging depth"), light source beamwidth, scan pivot location, and focal plane location. For reference, axial direction refers to a direction extending along, or parallel to, an axis that extends from a center of a front of the eye to a rear of the eye. Axial resolution correlates to a smallest size imaging feature, in an axial direction, that can be resolved. Image depth correlates to an axial distance across which satisfactory image data can be resolved. Light source beamwidth affects depth of field, which is a distance in the axial direction across which satisfactory focus can be obtained. Scan pivot location affects field of view. Field of view is an extent of an angle across which imaging data can be obtained. Therefore, field of view determines an extent of a distance, perpendicular to the axial direction, across which satisfactory imaging can be obtained.

Optimal analysis of the retina, anterior segment, and biometry features of interest can involve different optical arrangements because of the different dimensions of features to be analyzed. Specifically, retina imaging involves high axial resolution over a shorter image depth. Anterior segment analysis can be made with relatively lower resolution but may involve a longer image depth than retina imaging, and higher axial resolution than biometry. Biometry feature analysis, of an axial eye length in particular, can involve a long image depth, specifically an entire length of the eye, which may compromise axial resolution. Biometry can include measurement of various ophthalmic features such as, by example and without limitation, axial length, corneal radii, anterior chamber depth, lens thickness, central corneal thickness, white to white, etc.

Historically, different types of techniques have been employed to perform the above-described types of analyses separately, using ultrasound or optical imaging involving, for example, keratometry for cornea analysis, low coherence interferometry for axial length measurements, and OCT for retina imaging and anterior imaging. In time, combination devices became available that combined keratometry and narrow bandwidth swept source and OCT devices operating with fixed configurations. Each of such arrangements are separately optimized for desired optical resolution, image depth and other optical parameters suited for the corresponding type of analysis. The respective separate arrangements cannot be dynamically tuned from one analysis type to another.

The current state-of-the-art has endeavored to utilize OCT techniques for each of the imaging modes by configuring for an optimum desired axial resolution for a given modality. This means the quality of imaging will be compromised. For example, for an imaging device optimized for retinal imaging, the imaging device will be optimized for maximum axial resolution and by moving an optical delay line by a known step size to achieve sufficient imaging depths for other modes. Such arrangements typically suffer from quality deficiencies, increased complexity, and cost, as they may require or suffer from the need to employ additional/excess processing steps, additional uncertainty associated with measurement results, and expensive precision components. In addition, compromised analysis quality results in less effective evaluation, diagnosis and treatment.

In view of the foregoing and other limitations, a multimode eye analysis system, method, and computer readable medium according to example aspects herein are provided that enable a plurality (e.g., at least three) of types of eye analysis to be provided by a single evaluation device, substantially without compromising imaging quality and while using substantially the same components to reduce system complexity and cost as compared to prior art systems. By virtue thereof, the system herein can be adaptably and dynamically tuned to provide superior analysis for each of the plurality of eye analysis types, including, for example, at least retina imaging, anterior segment imaging, biometry imaging, and, in some example embodiments herein, other diagnostics as well.

According to an example aspect herein, each or at least some of the axial resolution, image depth, light source beamwidth, scan pivot location, and focal plane location is dynamically adjustable alone or in conjunction with one another in order to be optimized for multiple different eye analysis modes. This optimizing is accomplished without the need for separate significant systems and elements for different modes, and substantially without compromising analysis quality, even though each mode may rely on the same or similar core system elements.

FIGS. 1A-1F illustrate examples of scans showing different optical parameters suitable for different eye analysis modes. For reference, an axial direction refers to the direction extending along, or parallel to, an axis extending from a center of a front of the eye to a rear of the eye, as represented, for example, by arrowed line 101 in FIGS. 1A-1C.

FIG. 1A illustrates eye cross section 105, including cornea 115, pupil 133, lens 110 and retina 120. FIG. 1A also illustrates optical parameters suitable for retinal imaging analysis (also referred to herein as a retina scan mode or retina mode). Specifically, (imaginary) box 125 indicates an image depth represented by distance 130. Image depth 130 is sufficient to encompass a thickness of retina 120. A lateral extent of a field of view, in particular, distance 135, also is illustrated. Distance 135 is sufficient to encompass a lateral dimension of retina 120. In this illustrated embodiment, distance 135 also represents a scan width (and accordingly, the image width) and lateral depth of field. However, it will be recognized that in other examples different lateral fields of view may be utilized. FIG. 1A also illustrates scan pivot location 140, also referred to as a beam pivot, which is positioned at a center of the pupil 133. The location of scan pivot 140 determines the lateral extent of the field of view (e.g., distance 135), because field of view is determined by the diverging angle of view 119 originating at scan pivot location 140. In addition, FIG. 1A illustrates predetermined focal plane 145, which is an axial location of sharpest focus. Focal plane 145 can be adjusted along the axial direction 101 during imaging by an adjustable optical parameter unit to be more fully described below with reference to FIGS. 3 and 4A—4C.

FIG. 1A also illustrates a retina scan mode axial resolution indicated by hashmarks 172. As will be discussed in more detail below, an axial resolution for imaging in the retina scan mode (FIG. 1A) is a higher resolution than an axial resolution for imaging in the anterior segment scan mode (FIG. 1B). Similarly, an axial resolution for imaging in anterior segment scan mode (FIG. 1B) is a higher resolution than an axial resolution for imaging in the biometry scan mode (FIG. 1C). Differences in example resolutions for different modes is represented by the narrow-spaced hashmarks 172 associated with the retina scan mode illustrated by FIG. 1A, compared to less narrow-spaced hashmarks of an anterior segment scan mode axial resolution 174 associated with the anterior segment scan mode illustrated by FIG. 1B, and compared to even less narrow-spaced hashmarks of biometry scan mode axial resolution 176 associated with the biometry scan mode illustrated by FIG. 1C. Transition from lower resolution 176 to higher resolution 174, and/or to even higher resolution 172, can be referred to as axial resolution zoom, axial zoom, "zoom in", or "zooming in". Transition from higher resolution 172 to lower resolution 174, and/or to even lower resolution 176, can be referred to "zoom out" or "zooming out".

As will be described in more detail below, according to an example aspect herein, each, or at least some of the parameters such as image depth, light source beamwidth, scan pivot location, and focal plane location can be dynamically adjusted alone or in conjunction with one another to be made suitable for different types of eye analysis modes. Moreover, in addition to these parameters, an axial resolution can be dynamically adjusted as well, alone or in conjunction with the other parameters, wherein axial resolution adjustment can determine both the axial resolution (e.g., 172, 174 and 176) and the image depth (e.g., 130, 155 and 162). In addition, as will be described in more detail below with reference to FIG. 3, a reference light path distance (e.g., length) can be varied to locate (imaginary) box 125, 150, and/or 186 and thereby its associated optical parameters along the axial direction 101. For example, varying a reference light path distance can move box 125 from a retina area in FIG. 1A, to an anterior segment area, shown as (imaginary) box 150 shown in FIG. 1B, and/or to (imaginary) box 186 shown in FIG. 1C (or FIG. 1D, 1E, 1F), or in another order than described. Moreover, finer variations of a reference light path facilitate imaging across a full width of the image depth (e.g., 130, 155 and 162). A size and shape of each (imaginary) box 125, 150, 186 can be determined based on at least one of a sweep bandwidth (e.g., sweep bandwidth 309 described below) or the reference light path distance, in one example embodiment herein.

FIG. 1B illustrates eye cross section 105, including cornea 115, pupil 133, lens 110 and retina 120. FIG. 1B illustrates optical parameters suitable for anterior segment analysis (also referred to herein as an anterior mode, anterior segment mode, or anterior segment scan mode). An anterior segment 156 of eye 105 comprises at least cornea 115, pupil 133, lens 110 and a region behind lens 110. Thus, anterior segment 156 comprises a front portion of eye 105. Box 150 indicates an image depth represented by distance 155. Image depth 155 is wider than image depth 130 (FIG. 1A), encompassing substantially the full anterior portion, in particular, anterior segment 156, of eye 105. A lateral extent of a field of view, in particular, distance 157, also is illustrated. Distance 157 is sufficient to encompass a lateral dimension of anterior segment 156. In this illustrated embodiment, distance 157 also represents the light source beamwidth. As noted, in other examples, scan width and field of view may be different than those shown. Scan pivot location 159 is located at a position in front of the eye 105. Focal plane 161 is located inside image depth 155 and can be adjusted along the axial direction 101 during imaging by an adjustable optical parameter unit to be more fully described below with reference to FIGS. 3 and 4A-4C.

FIG. 1C illustrates eye cross section 105, including cornea 115, pupil 133, lens 110 and retina 120. FIG. 1C illustrates optical parameters for the biometry imaging mode (also referred to herein as the biometry mode or biometry scan mode). Box 186 indicates an image depth represented by distance 162. Image depth 162 can be adjusted to encompass substantially an entire length of the eye 105. A lateral extent of a field of view (e.g., a lateral depth of field), in particular, distance 164, also is illustrated. In this illustrated embodiment, distance 164 also represents the light source scan width. The distance 164 (i.e., the scan width and field of view) can be adjusted to be relatively narrower (or wider), thereby increasing (or decreasing) depth of field, which is useful for the biometry mode. Specifically, an increased depth of field increases the axial distance over which good focus is obtained for a particular focal plane location. In some example embodiments herein, the biometry mode may involve imaging an entire length of eye 105. Therefore, an increased depth of field can be desirable. Scan pivot 166 is located just in front of pupil 133. Focal plane 163 is located within image depth 162. Focal plane 163 can be adjusted along the axial direction 101 during imaging by an adjustable optical parameter unit to be more fully described below with reference to FIGS. 3 and 4A—4C.

FIG. 1D illustrates an alternate configuration of optical parameters suitable for the anterior segment mode. Specifically, impinging light 168 can be adjusted to be telecentric (as shown), rather than converging.

FIG. 1E illustrates an alternate configuration of optical parameters suitable for the biometry mode. Specifically, scan pivot 170 is located near a center of the length of the eye 105.

FIG. 1F illustrates an alternate configuration of optical parameters suitable for the biometry mode. Specifically, impinging light 172 can adjusted to be telecentric (as shown), rather than converging.

According to an exemplary aspect herein, scans according to at least some, or all, of FIGS. 1A-1F can be employed or obtained by the multimode eye analysis system 300 of FIG. 3 to be described below. Before describing FIG. 3, FIGS. 2A-2C will first be described.

Figure 2B:
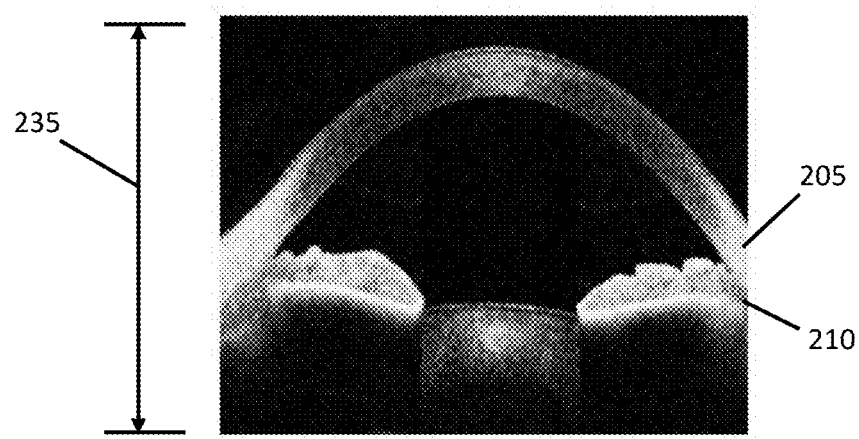
FIG. 2B shows an example anterior segment image obtained in an anterior segment mode.
Figure 2C:
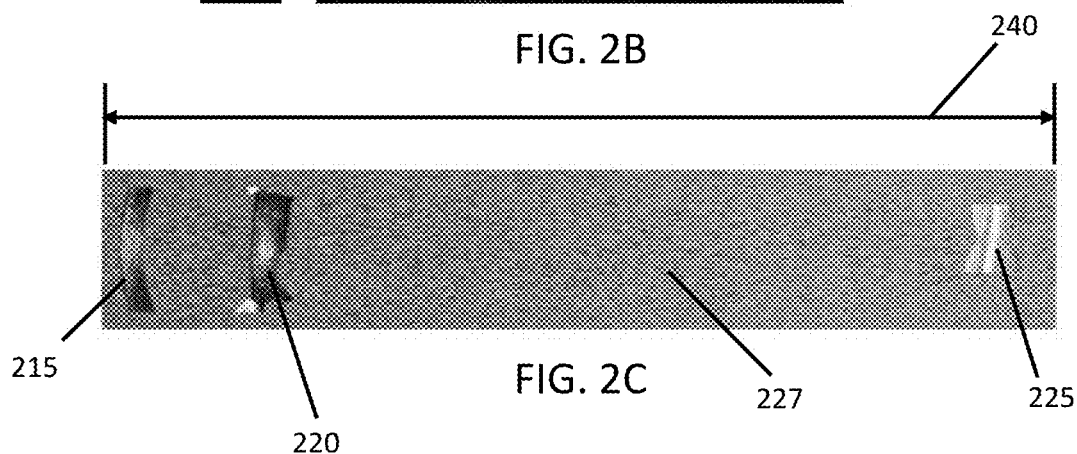
FIG. 2C shows an example biometry image obtained in a biometry mode.

FIGS. 2A-C are examples of images obtained by the system 300 (and displayed by user interface 380 thereof) while operating in the retina mode, anterior segment mode, and biometry mode, respectively. Specifically, portion 203 of image FIG. 2A is an example image of a cross section of retina tissue obtained in the retina mode. FIG. 2B is an example image of a cross section of an anterior segment (e.g., segment 156) obtained in the anterior segment mode. FIG. 2B shows anterior segment features including cornea 205 and iris 210. FIG. 2C is an example image of a cross section (a central slice) of an entire length of the eye (from a front of the eye to a back of the eye) obtained in the biometry mode, and illustrates a central portion of an eye length. FIG. 2C shows cornea portion 215, lens portion 220, and retina portion 225. An area extending between lens portion 220 to retina portion 225 comprises sample vitreous portion 227.

Each of the imaging modes corresponding to FIGS. 2A, 2B and 2C, namely the retina mode, anterior segment mode, and biometry mode, respectively, benefits from different respective image resolutions and image depths. An exemplary image depth 230 for the retina mode (FIG. 2A) is 5.6 millimeters, an exemplary image depth 235 for anterior segment mode (FIG. 2B) is 8.2 millimeters, and an exemplary image depth 240 for the biometry mode (FIG. 2C) is 32 millimeters. These examples are merely illustrative in nature, and not limiting to the scope of the invention.

Each respective mode also may benefit from, or can tolerate, different imaging axial resolutions. By example, owing to relatively smaller geometries of the retina (involved in the retina mode) as compared to the anterior segment and biometry modes, a high axial resolution can be beneficial for the retina mode. An exemplary axial resolution for the retina mode is 5 micrometers. An exemplary axial resolution for the anterior segment mode is 7.1 micrometers. An exemplary axial resolution for biometry mode is 27 micrometers. These examples are merely illustrative in nature, and not limiting to the scope of the invention.

Example embodiments herein employ optical coherence tomography (OCT) techniques for eye analysis, although that example is not limiting. Basic properties and an example of the manner in which of OCT systems operate are disclosed in a publication by Josef Bille, entitled *High Resolution Imaging in Microscopy and Ophthalmology*, Springer Nature Switzerland AG., 2019, including Chapter 3, pages 59-86 ("the Bille publication"), the contents of which are hereby incorporated by reference herein in their entirety as if set forth fully herein. OCT operates by combining light returning from a sample under examination with reference light derived from the same originating light source. The combined light is converted to a digital signal which, in turn, is converted to image information representing an appearance of the sample at a distance (into the sample) corresponding to a length a reference light path (also referred to as a reference arm). The reference light path is the path that the reference light traverses from the originating light source to a detector which converts light to digital information, which is then converted to the image information. The light travelling from the originating light source along a sample arm to the sample, and traveling back along the sample arm to the detector, is referred to as sample light. The length of the reference light path (reference arm) is actively varied so as to enable imaging through an entire depth of the sample. As a result, an image can be obtained of a cross section of the sample at a point where the sample light impinges the sample. The sample light is scanned side to side and up and down to obtain a full three-dimensional image throughout the sample.

Figure 3:
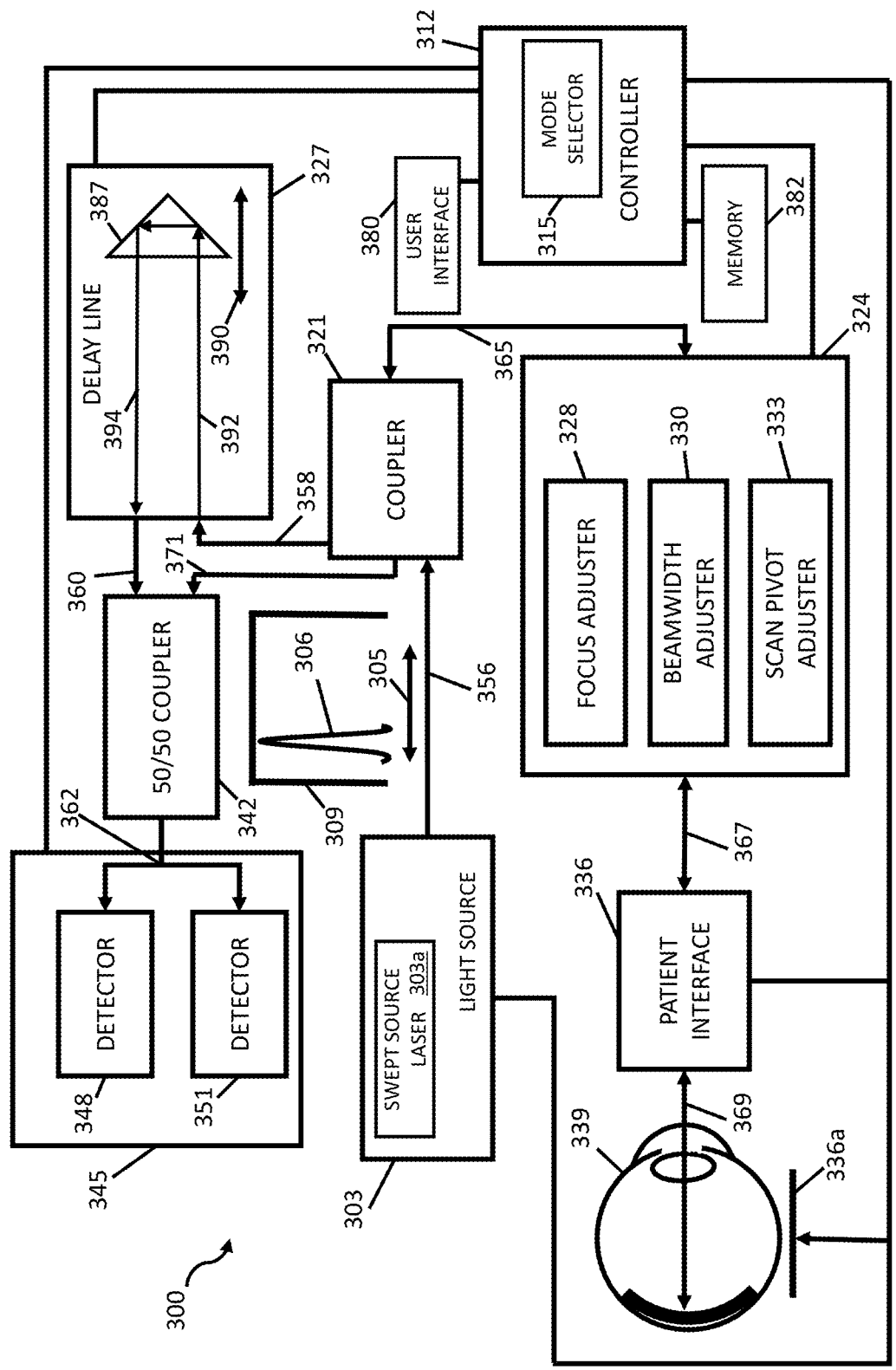
FIG. 3 is a block diagram of an embodiment of a multimode eye analysis system constructed and operated according to an example embodiment herein.

FIG. 3 will now be described in more detail. FIG. 3 is a block diagram of multimode eye analysis system 300 constructed and operated according to an example embodiment herein. The system 300 includes, according to an example aspect herein, an adjustable light source 303 that comprises a swept source laser 303a. The swept source laser 303a emits light (e.g., coherent light or coherence light) having a wavelength 306 that can be controllably varied, e.g., by controller 312, so as to be swept across a sweep bandwidth 309, as represented by arrow 305. In one non-limiting example embodiment herein, a swept source laser device is employed as 303a, and the adjustable light source 303 comprises a super-luminescent diode (SLD), although these examples are not limiting. A center wavelength of the sweep bandwidth 309 is 1060 nanometers, in one example embodiment herein. The sweep bandwidth 309 also can be controllably varied under control of controller 312 to be made wider or narrower. In one example embodiment herein, a frequency of the light emitted by the light source 303 is fixed at a predetermined frequency, under control of controller 312, while the sweep bandwidth 309 is controllably varied by the controller 312 to determine at least in part, the axial resolution of the system 300 during scanning, as well as the image depth during scanning. Also, in one example embodiment herein, the sweep bandwidth 309 ranges from 18 nanometers to 100 nanometers, as determined by controller 312. Further in an example embodiment herein, the sweep is +/−9 nanometers to +/−50 nanometers with respect to the center wavelength, as determined by controller 312. As mentioned, the width of sweep bandwidth 309 can determine, at least in part, the axial resolution of the system 300 during scanning, as well as the image depth during scanning. In one example embodiment herein, axial resolution increases as sweep bandwidth 309 increases. Because sweep bandwidth 309 is variable, and can be set by controller 312, different axial resolutions and image depths can be selected by the controller 312 for different eye analysis modes. In one example embodiment herein, relationships between a sweep bandwidth, axial resolution, and/or image depth can be in accordance with those defined in the Bille publication, although this example is not limiting to the scope of the invention.

The controller 312 comprises mode selector 315. According to an example aspect herein, the mode selector 315 can select, and/or be operated to select, at least one of a plurality of available operating modes of the system 300, such as, by example, the retina mode, the anterior segment mode, the biometry mode, or other imaging modes, and also a submode within one or more of those modes, such as a diverging mode (e.g., FIG. 1A, 1B, 1C, or 1E) or a telecentric mode (e.g., FIG. 1D or 1F). The controller 312 is coupled to user interface 380, memory 382, delay line 327, detector 345, light source 303, patient interface 336, stage 336a, and optical parameter adjustment unit 324.

In an example embodiment herein, patient interface 336 includes an objective lens or another type of examination equipment through which sample light from the optical parameter adjustment unit 324 can scan the sample 336, although, in other example embodiments, no patient interface 336 need be provided in the system 300. Also in one example embodiment herein, the stage 336a is an alignment stage that can arrange a position of the patient's head and/or eye, under control of the controller 312 based on, for example, the mode selected by the mode selector 315. Also in an example embodiment herein, user interface 380 includes one or more input and/or output user interfaces that enable a user to input information into the controller 312 and/or perceive outputted information. By example and without limitation, the user interface 308 can include one or more of a keyboard, a keypad, a computer mouse, joy stick, a touchscreen, a visual display, a printer, and a speaker, and the like.

Figure 6:
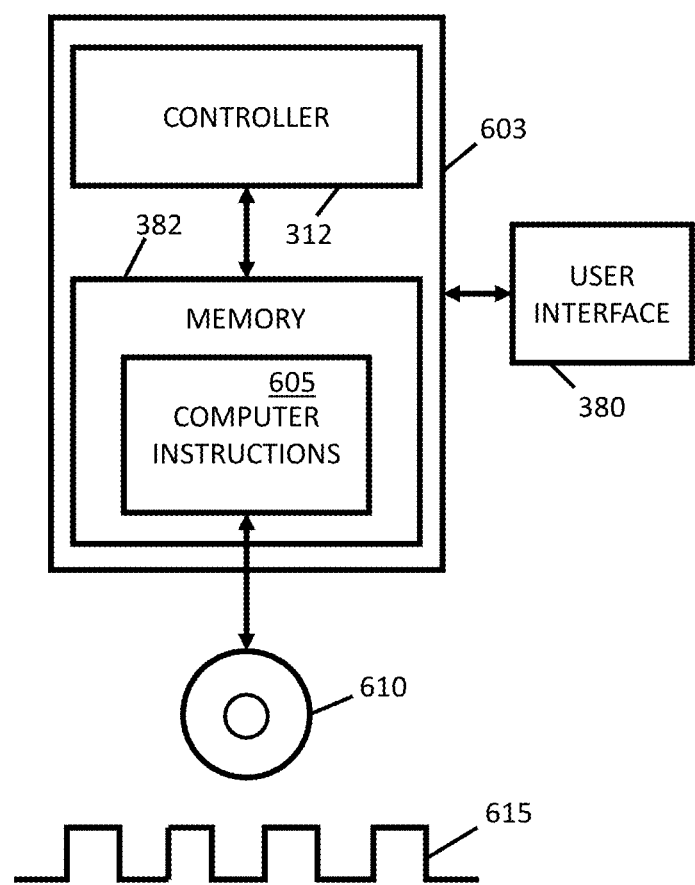
FIG. 6 is a block diagram of components of a multimode eye analysis system according to an example embodiment herein.

Referring briefly to FIG. 6, the controller 312 and memory 382 are shown within a digital component module 603, coupled to user interface 380 and a storage medium 610. In an example embodiment herein, controller 312 comprises a digital microprocessor capable of executing computer programming instructions and operating on computer data, although in other embodiments controller 312 can be hardcoded with logic. Memory 382 comprises a computer readable memory or storage medium that stores computer executable instructions 605, executable by controller 312, to carry out operations and procedures of system 300, including those described herein and shown in the Figures. In an example embodiment herein, memory 382 comprises a ROM (e.g., in the form of an electrically-erasable programmable read-only memory (EEPROM) or flash memory) which is pre-loaded with computer-readable instructions 605, and/or a RAM or similar type of memory. Computer-readable instructions 605 can be provided to memory 382 from a computer program product, such as a non-transitory, computer-readable storage medium 610 in the form of a CD-ROM, DVD-ROM, floppy disc, etc. or a computer-readable signal 615 carrying the computer-readable instructions 605. Controller 312 interacts with memory 382 to execute the computer instructions 605. Memory 382 can also collect and store for manipulation, processing and display, image data collected by controller 312 (e.g., from detector 345 of FIG. 3).

Referring again to FIG. 3, adjustable light source 303 is communicatively coupled at its output to optical coupler 321, by way of path 356. Coupler 321 splits light emanating from light source 303 into reference light and sample light, wherein the reference light is directed along a reference path (or reference arm) formed by path 358, delay line 327, path 360, coupler (e.g., a 50/50 coupler) 342, and detector 345, and wherein the sample light is directed along a sample path (or sample arm) formed by path 365, optical parameter adjustment unit 324, path 367, interface 336, path 369, and eye 339. Each path 356, 365, 367, 369, 358, 360, 367, 369, 371, 392, 394, is an optical path for communicating light, and may include any suitable type of optical path such as, by example only, optical fiber, and, in the case of paths 367 and 369, a non-fiber interface.

With regard to the sample light provided from coupler 321, the sample light travels through the optical parameter adjuster unit 324 and through patient interface 336, impinges on the sample 339, and is reflected back from the sample 339 such that it returns back along the sample arm, and passes back through coupler 321 to coupler 342 of the reference arm.

With regard to the reference light, the reference arm through which that light passes is variable by virtue of the delay line 327, under control of the controller 312. More particularly, in an example embodiment herein controller 312 varies the length of the reference arm by variably positioning a mirror 387 of the delay line 327 laterally along a direction indicated by arrow 390, thereby varying lengths of light paths 392 and 394 of delay line 327, and thus also varying the overall length of the reference arm. In an example embodiment herein, the delay line 327 is controlled by controller 312 so that the length of the reference arm is equal to a distance or depth into sample 339 at which the sample light impinges the sample 339 for scanning an image thereof. The length of the reference arm can be varied such that corresponding variations of the mentioned distance into the sample 339 can be specified accordingly. By example and without limitation, the delay line 327 (and reference arm) can be controlled by controller 312 such that a scan can be taken at a location within (imaginary) box 125 and image depth 130 represented in FIG. 1A, in a case where the retina mode is selected by the mode selector 315. Also by example, the delay line 327 (and reference arm) can be controlled by controller 312 such that a scan can be taken at a location within (imaginary) box 150 and image depth 155 represented in FIG. 1B, in a case where the anterior mode is selected by the mode selector 315. Further by example, the delay line 327 (and reference arm) can be controlled by controller 312 such that a scan can be taken at a location within (imaginary) box 186 and image depth 162 represented in FIG. 1C, in a case where the biometry mode is selected by the mode selector 315. Thus, according to an example aspect herein, within each separate one of the modes, the sample light can scan the sample 339 side to side and up and down, in conjunction with the varying of lengths of the reference arm based on the depths of the scanning distance into the sample 339, thereby enabling a full scanning image (e.g., 2D or 3D) to be obtained of an entire corresponding portion of the sample 339 being imaged by the mode. Also, when this is performed for each mode, a full scanning image (e.g., 2D or 3D) of the entre sample 339 can be obtained, including images of the portions imaged by respective ones of the modes.

Referring now to coupler 342, that component combines the sample light received from coupler 321 with the reference light received from delay line 327. When the length of the reference arm is equal to the distance into sample 339 at which the sample light scans the sample 339, the combined light forms an interference wave pattern that is then forwarded to the detector 345 by way of node 362. In one example embodiment herein, control of the delay line 327 (and thus control of a length of the reference arm) by the controller 312 can be performed in accordance with a technique for varying a reference arm as described in the Bille publication, although that example is not limiting.

In the illustrated example embodiment, the detector 345 is a balanced detector that comprises a plurality of detectors, such as detectors 348 and 351. However, in other example embodiments herein, another type of detector can be used instead, or, in still other example embodiments herein, more or less than two detectors can be employed in the detector 345. Detector 345 converts the interference wave pattern, which is an optical signal, into an electrical signal which is then provided to controller 312 wherein the signal is processed into digital information, and subsequently into image information representing an image. In one example embodiment herein, use of the two detectors 348 and 351 in the detector 345 results in an improved signal-to-noise ratio of the electrical signal generated by detector 345. In one example embodiment herein, detector 348 and detector 351 comprise respective photodiodes connected in series such that their photocurrents cancel one another out when they are equal. Such an arrangement eliminates or substantially minimizes a common mode signal, thereby improving the signal-to-noise ratio. Also, in one example embodiment herein, the output of coupler (e.g., 50/50 coupler) 342 includes two outputs, one of which is coupled to an input of detector 348 and another of which is coupled to an input of detector 351, although for convenience only a single output line is depicted as extending from the coupler 342 to detector 345 in FIG. 3.

The controller 312 can store the image in the memory 382 and/or storage medium 610, and/or can cause it to be presented (e.g., displayed) via user interface 380. By virtue of the system 300, an entire depth of sample 339 can be scanned to obtain a full three-dimensional scan of the entire sample 339.

An example aspect of herein will now be described. According to this example aspect, the system 300 is controllable by the controller 312 to be placed in one of a plurality of available modes for obtaining images, based on the type of mode selected by the mode selector 315. In one example embodiment herein, the plurality of modes include the retina mode, the anterior segment mode, and the biometry mode, and each establishes a respective focal plane for obtaining images in the corresponding mode. Also, in one example embodiment herein, such controlling can involve the controller 312 controlling/specifying at least one bandwidth of the system 300. For example, the controller 312 can control the sweep bandwidth of the light source 303 and/or a bandwidth of the adjustable optical parameter unit 324 based on the type of mode selected by the mode selector 315. With respect to the light source 303, the controller 312 can control the light source 303 such that the sweep bandwidth 309 emitted thereby has a first predetermined bandwidth (e.g., 100 nm) in a case where the retina mode is selected by the mode selector 315, a second predetermined bandwidth (e.g., 70 nm) in a case where the anterior segment mode is selected by the mode selector 315, and a third predetermined bandwidth (e.g., 18 nm) in a case where the biometry mode is selected by the mode selector 315. According to one example embodiment herein, and with respect to the bandwidth of the adjustable optical parameter unit 324, the controller 312 can control the adjustable optical parameter unit 324 such that a spectral range (e.g., a bandwidth) covered by the adjustable optical parameter unit 324 (and thus the spectral range in which light is detected by the detector 345) is within (i) a fourth predetermined bandwidth (e.g., spectral range) in a case where the retina mode is selected by the mode selector 315, (ii) a fifth predetermined bandwidth (e.g., spectral range) in a case where the anterior segment mode is selected by the mode selector 315, and (iii) a sixth predetermined bandwidth (e.g., spectral range) in a case where the biometry mode is selected by the mode selector 315. As a result, the spectral range in which light can be detected by the detector 345 during the selected mode also is within the selected predetermined bandwidth.

In one example embodiment herein, the first predetermined bandwidth and the fourth predetermined bandwidth correspond to one another and can be the same, the second predetermined bandwidth and the fifth predetermined bandwidth correspond to one another and can be the same, and the third predetermined bandwidth and the sixth predetermined bandwidth correspond to one another and can be the same, although in other example embodiments herein they can be different from one another. Also, in one example embodiment herein, the controller 312 controls/specifies the at least one bandwidth of the system 300 by controlling only the sweep bandwidth of the light source 303 based on the selected mode, but not the bandwidth of the adjustable parameter unit 324. In another example embodiment herein the controller 312 controls/specifies the at least one bandwidth of the system 300 by controlling only the bandwidth of the adjustable optical parameter unit 324 based on the selected mode, but not the sweep bandwidth of the light source 303. In still another example embodiment herein, the controller 312 controls/specifies the at least one bandwidth of the system 300 by controlling both the bandwidth of the adjustable optical parameter unit 324 and the sweep bandwidth of the light source 303, based on the selected mode.

In the illustrated example embodiment shown in FIG. 3, the adjustable optical parameter unit 324 comprises focus adjuster 328, beamwidth adjuster 330, and scan pivot adjuster 333. With respect to the focus adjuster 328, that element enables the adjustable optical parameter unit 324 to be adjusted to (a) establish one or more focal planes, such as, by example, focal planes 145, 161 and/or 163, and/or (b) adjust the bandwidth covered by the focus adjuster 328 (and thus the bandwidth of the optical parameter unit 324), based on the mode selected by the mode selector 315. More particularly, with respect to capability (a), focus adjuster 328 is controllable by controller 312 to determine a location of a focal plane along an axial direction within the sample (e.g., eye) 339. For example, focus adjuster 328 can establish focal planes 145, 161 and/or 163 (FIGS. 1A, 1B, 1C), respectively, at respective predetermined desired locations in the sample 339, depending on which mode is selected by mode selector 315. With respect to capability (b), which also is referred to herein as a zoom (zoom in or zoom out) capability, focus adjuster 328 is controllable by the controller 312 to establish, from among a plurality of bandwidths, the bandwidth covered by the focus adjuster 328 (and thus the bandwidth covered by the adjustable optical parameter unit 324), based on the mode selected by the mode selector 315. In one example embodiment herein, the plurality of predetermined bandwidths include the fourth predetermined bandwidth, the fifth predetermined bandwidth, and the sixth predetermined bandwidth. The bandwidth covered by the adjustable optical parameter unit 324 determines the spectral range in which light is detected by the detector 345 during the selected mode.

Focus adjuster 328 can be adjusted to move or adjust focal planes 145, 161 and/or 163, and/or to adjust the bandwidth covered by the optical parameter unit 324 by, for example, moving at least one objective lens (not shown in FIG. 3) included in focus adjuster 328 along the sample arm to a predetermined position corresponding to the selected mode, and/or by introducing, adjusting, or removing optical lenses in the sample arm, according to the selected mode. In another example, the focal planes 145, 161 and/or 163 and/or the bandwidth individually can be adjusted by virtue of the controller 312 adjusting position(s) of one or more of the sample 339 by way of stage 336a, the interface 336, and/or the objective lens, relative to each other, based on the selected mode.

According to one example embodiment herein, the focus adjuster 328 operates, at least with respect to providing capability (a) referred to above, in a manner as described in the publication by Michelle Cua et al., entitled "Retinal optical coherence tomography at 1 μm with dynamic focus control and axial motion tracking", Journal of Biomedical Optics 21(2), February 2016, pp. 026007-1 to 026007-8 ("the Cua publication"), which is incorporated by reference herein in its entirety as if set forth fully herein. Also, in one non-limiting example embodiment herein, objective lens 408 (to be described below in conjunction with FIG. 4A) can be included in the focus adjuster 328, and itself can include, at least in part, a variable focus lens such as a variable focus liquid lens (VL), an acousto-optic tunable lens, an axicon lens, or adaptive optics, described in the Cua publication, and the objective lens can be dynamically focused as described in that publication. The foregoing example embodiments are not exclusive, and, in other example embodiments herein, other types of objectives and lens control/operation techniques can be employed.

Also, as described above, in one example embodiment herein the focus adjuster 328 has the zoom capability (capability (b) described above). In that example embodiment herein, the focus adjuster 328 includes a lens system that provides the zoom capability. One example of a lens system that can be employed in the focus adjuster 328 is described in the publication by J. Choi et al., entitled "Zoom lens design for a novel imaging spectrometer that controls spatial and spectral resolution individually", Applied Optics, Vol. 45, No. 15, May 20, 2006, pp. 3430 to 3441, which is incorporated by reference herein in its entirety as if set forth fully herein.

Figure 8A:
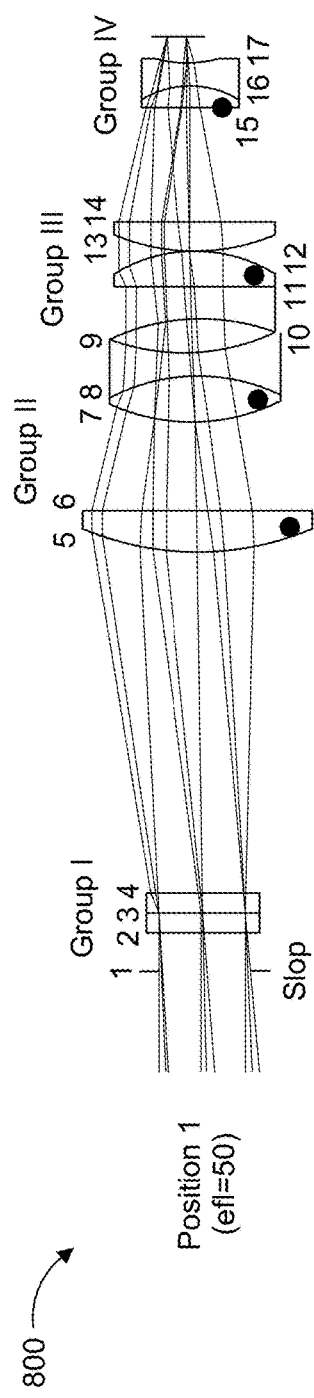
FIG. 8a shows an example lens system disposed in a Position 1, that can be employed in the multimode eye analysis system of FIG. 3, according to an example embodiment herein.
Figure 8B:
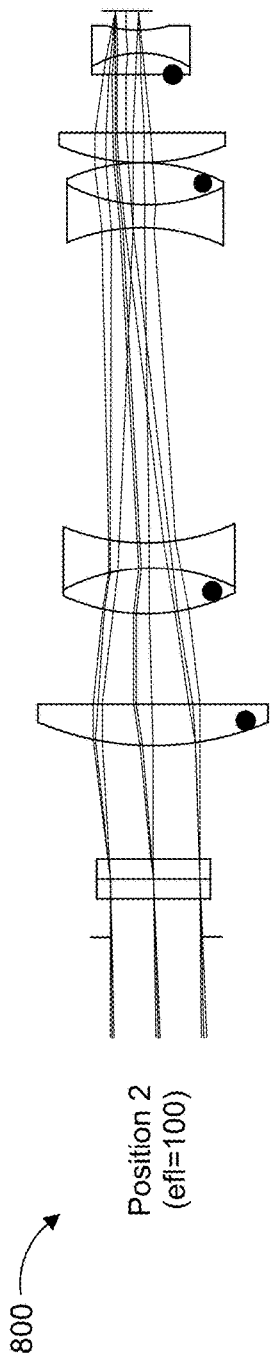
FIG. 8b shows an example lens system disposed in a Position 2, that can be employed in the multimode eye analysis system of FIG. 3, according to an example embodiment herein.
Figure 8C:
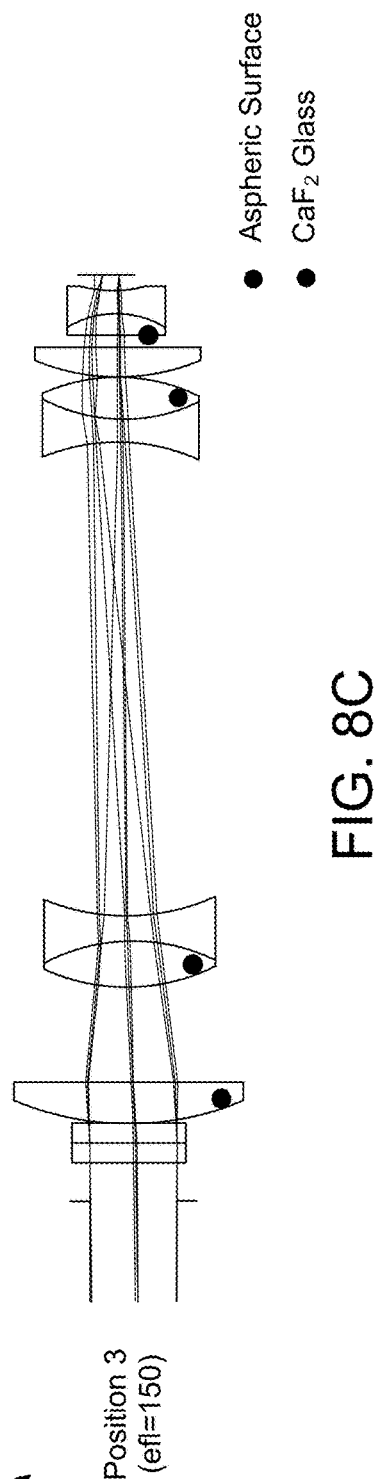
FIG. 8c shows an example lens system disposed in a Position 3, that can be employed in the multimode eye analysis system of FIG. 3, according to an example embodiment herein.

FIGS. 8a, 8b, and 8c herein depict an example of a lens system 800 that can be employed in the focus adjuster 328. In one example embodiment herein, the objective lens 408 (FIG. 4A) of the focus adjuster 328 includes the lens system 800. Also in one example embodiment herein, at least some of components of the lens system 800 and the above-described components of the Cua publication are the same, although in other example embodiments the components can be separate from one another. In FIG. 8a the lens system 800 is represented as being disposed in a Position 1, in FIG. 8b the lens system 800 is represented as being disposed in a Position 2, and in FIG. 8c the lens system 800 is shown as being disposed in a Position 3.

The controller 312 determines the position (e.g., Position 1, Position 2, or Position 3) in which the lens system 800 is disposed. In an example embodiment herein, Position 1 covers a field of view of 12.0 degrees and a predetermined spectral bandwidth range (e.g., a fourth predetermined bandwidth), Position 2 covers a field of view of 5.9 degrees and another predetermined spectral range (e.g., a fifth predetermined bandwidth), and Position 3 covers a field of view of 3.9 degrees and a further predetermined spectral bandwidth range (e.g., a sixth predetermined bandwidth). If the lens system 800 or a transmission grating are rotated, the spectral ranges of Positions 2 and 3 vary at least somewhat from the mentioned corresponding predetermined spectral bandwidth ranges. In another example embodiment herein, at least one of the fourth, fifth, or sixth predetermined bandwidths, or, in another example embodiment herein, a total range of such bandwidths together, is from 780 nm to 920 nm, centered at 850 nm. Of course, these examples, and the example positions of the lens system 800 represented in FIGS. 8a, 8b, and 8c, are merely illustrative in nature, and are not intended to be limiting to the scope of the invention.

Beamwidth adjuster 330 of unit 324 is controllable by controller 312 to narrow or widen a beamwidth of the sample light scanning the sample 339, based on the mode selected by the mode selector 315. By example, the beamwidth adjuster 330 can be controlled by the controller 312 such that the sample light scans the sample 339 using a beamwidth (e.g., 135, 157, 164) (FIGS. 1A, 1B, 1C) (and/or a beamwidth represented in FIG. 1D, 1E, 1F) that corresponds to the mode (and sub-mode, if any) selected by the mode selector 315.

In one example embodiment herein, adjustment of the beamwidth can include moving an objective lens (not shown in FIG. 3) of the beamwidth adjuster 330 along the sample arm to a predetermined position corresponding to the selected mode (and sub-mode, if any), and/or introducing predetermined additional optical elements into the sample arm, according to the selected mode (and sub-mode). In another example embodiment herein, the beamwidths 135, 157 and 164 (FIGS. 1A, 1B, 1C) (and/or beamwidths represented in FIG. 1D, 1E, 1F) individually can be adjusted by the controller 312 adjusting position(s) of one or more of the sample 339 by way of stage 336a, the interface 336, and/or the objective lens, relative to each other, based on the selected mode. According to one example embodiment herein, components of the Cua publication described above, and/or the lens system 800 can be employed in the beamwidth adjuster 330. In one example embodiment herein, objective lens 417 (of FIG. 4B to be described below) can be included in the beamwidth adjuster 330, and the objective lens 417 can include those components of the Cua publication and/or the lens system 800. At least some components of the lens system 800 and the above-described components of the Cua publication can be the same, although in other example embodiments the components can be separate from one another. Moreover, although the objective lenses 408 and 417 are represented as being separate elements in FIGS. 4A and 4B, in some example embodiments herein they can be the same and/or include at least some of the same components.

In one example embodiment herein, the scan pivot adjuster 333 of unit 324 is controllable by controller 312 to determine a location of a scan pivot (or to determine that there is no scan pivot) based on the mode (and sub-mode) selected by the mode selector 315. For example, the controller 312 can establish at least one scan pivot, such as pivot 140, 159, 166 and/or 170 (FIGS. 1A, 1B, 1C, 1E), depending on the mode (and sub-mode, if any) selected by mode selector 315. In one example embodiment herein, in a case where the anterior mode is selected by the mode selector 315, a sub-mode (e.g., diverging or telecentric) also can be selected. In a case where the sub-mode selected by the mode selector 315 is a diverging sub-mode, then a diverging scan pivot such as that shown in, by example, FIG. 1B is established by the controller 312, whereas in a case where the sub-mode selected by the mode selector 315 is a telecentric sub-mode, then a telecentric scan such as that shown in, by example, FIG. 1D is established by the controller 312. In a case where the biometry mode is selected by the mode selector 315, a scan pivot such as that represented by scan pivot 166 in FIG. 1C can be selected by the mode selector 315 and established by controller 312, a scan pivot such as that represented by scan pivot 170 in FIG. 1E can be selected by the mode selector 315 and established by controller 312, or a telecentric scan such as that represented by FIG. 1F can be selected by the mode selector 315 and established by controller 312. Of course, these examples are merely illustrative in nature, and should not be construed as being limiting to the scope of the invention.

In one example embodiment herein, adjustment of the scan pivot adjuster 333 can include moving an objective lens (not shown in FIG. 3) along the sample arm to a predetermined position corresponding to the selected mode (and sub-mode), and/or introducing additional optical elements into the sample arm, according to the selected mode. In another example herein, the scan pivots (e.g., 140, 159, 166 or scan types represented in FIGS. 1D to 1F) can be individually adjusted/provided by the controller 312 adjusting position(s) of one or more of the objective lens, the sample 339 by way of stage 336a, and/or interface 336, relative to each other, according to the selected mode. According to one example embodiment herein, components of the Cua publication described above, and/or the lens system 800 can be employed in the scan pivot adjuster 333. Also in one example embodiment herein, the scan pivot adjuster 333 can include an objective lens 423 (of FIG. 4c to be described below), and the objective lens 423 includes those components of the Cua publication and/or the lens system 800. At least some of components of the lens system 800 and the above-described components of the Cua publication are the same, although in other example embodiments the components can be separate from one another. Moreover, although the objective lenses 408, 417, and 423 are represented as being separate elements in FIGS. 4A, 4B, and 4C, in some example embodiments herein at least two or more of them they can be the same and/or include at least some of the same components.

In accordance with another example embodiment herein, scan pivot can be adjusted to effect a scan pivot based on the selected mode (and sub-mode) by aligning the patient (including eye 339) (e.g., by way of stage 336a) and/or at least some components (e.g., a fixation target) of the system 300 relative to one another, and this adjustment can be performed under control by the controller 312 and/or by manual adjustment, whether or not scan pivot adjuster 333 is also employed to adjust/effect the scan pivot In view of the foregoing, the adjustable optical parameter unit 324 can be controlled by the controller 312 to adjust one or more of the focal plane, beamwidth, scan pivot, and type of scan (e.g., diverging or telecentric) of the sample light that scans the sample 339, based on the mode (and sub-mode) selected by the mode selector 315. Also, in one example embodiment herein, the adjustable parameter unit 324 can be controlled by the controller 312 to adjust the bandwidth (e.g., spectral range) covered by the focus adjuster 328 (and thus the bandwidth of the optical parameter unit 324) to a selected predetermined bandwidth, based on the mode selected by the mode selector 315. As a result of that example embodiment, the spectral range in which light can be detected by the detector 345 during the selected mode also is within the selected predetermined bandwidth.

In either case, the sample light outputted by the adjustable optical parameter unit 324 scans the sample 339 by way of interface 336 and paths 367, 369, and, as described above, light reflected from the sample 339 as a result of the scan travels back through the sample arm towards coupler 321.

Also, according to an example aspect herein, additional optical parameters can be determined by the controller 312 based on the mode selected by the mode selector 315. By example, the controller 312 can determine/establish axial resolution and image depth of a scan by controlling at least one bandwidth of the system 300 (e.g., the sweep bandwidth 309 of light source 303 and/or the bandwidth covered by the adjustable optical parameter unit 324), according to the selected mode. As examples, the controller 312 can control the sweep bandwidth 309 to the first predetermined sweep bandwidth and/or the adjustable optical parameter unit 324's bandwidth to the fourth predetermined bandwidth, such that a scan can be performed (and detected) with axial resolution 172 and associated image depth 130, in a case where the retina mode is selected (FIG. 1A). Also by example, the controller 312 can control the sweep bandwidth 309 to the second predetermined sweep bandwidth and/or the adjustable optical parameter unit 324's bandwidth to the fifth predetermined bandwidth, such that a scan can be performed (and detected) with axial resolution 174 and associated image depth 155, in a case where the anterior segment mode is selected (FIG. 1B). Additionally, the controller 312 can control the sweep bandwidth 309 to the third predetermined sweep bandwidth and/or the adjustable optical parameter unit 324's bandwidth to the sixth predetermined bandwidth, such that a scan can be performed (and detected) with axial resolution 176 and associated image depth 162, in a case where the biometry mode is selected (FIG. 1C). The controller 312 also determines the location of the focal plane of a scan.

As can be appreciated in view of the foregoing, the above system 300 can be operated in at least one of a plurality of available imaging modes, including at least the retina mode, anterior segment mode, and biometry mode, and also can provide a diverging scan, a telecentric scan, and/or scan pivots at selected locations. As such, the system 300 does not suffer from limitations associated with conventional systems that can operate in only a lesser number of modes and which lack the foregoing and above-described operational capabilities.

Figure 4A:
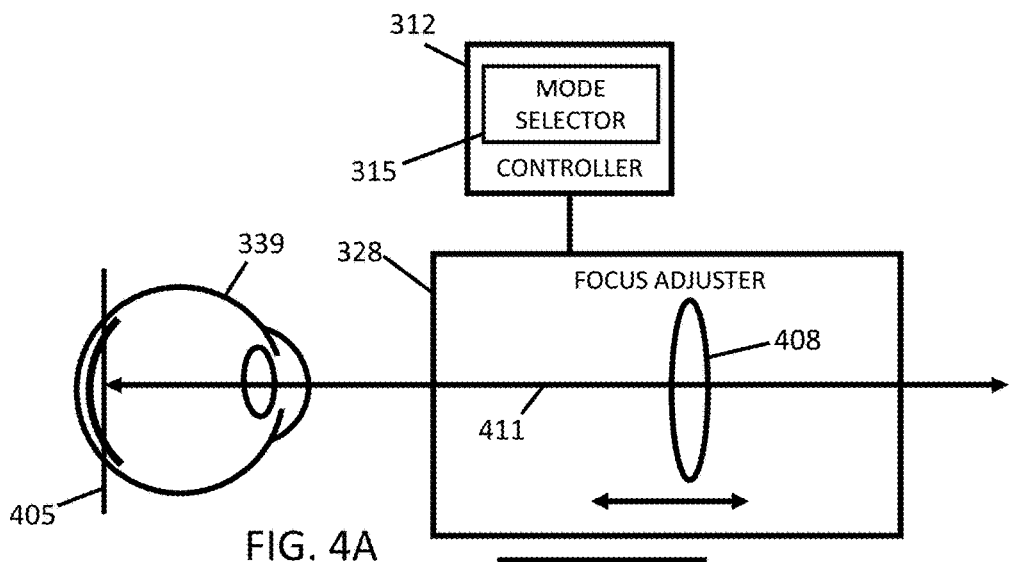
FIG. 4A is a diagram illustrating focus adjustment for an example embodiment herein of an adjustable optical parameter unit.

Having described the system 300 of FIG. 3, reference will now be made to FIGS. 4A-4C, which represent in greater detail examples of the manner in which the adjusters 328, 330 and 333, respectively, operate, according to one example embodiment herein using an objective lens. FIG. 4A illustrates an example embodiment of focus adjuster 328, and also shows eye 339 and controller 312. FIG. 4A also illustrates that a position of focal plane 405 can be adjusted by moving discrete lens (i.e., objective lens) 408 of focus adjuster 328 along light path (i.e., sample arm) 411. In one example embodiment herein, the controller 312 controls the movement of lens 408 based on the mode selected by the mode selector 315, in the manner described above in connection with FIG. 3. The foregoing example is not limiting, and, in other example embodiments herein, other techniques can be employed for positioning lens 408 and focal plane 405.

Figure 4B:
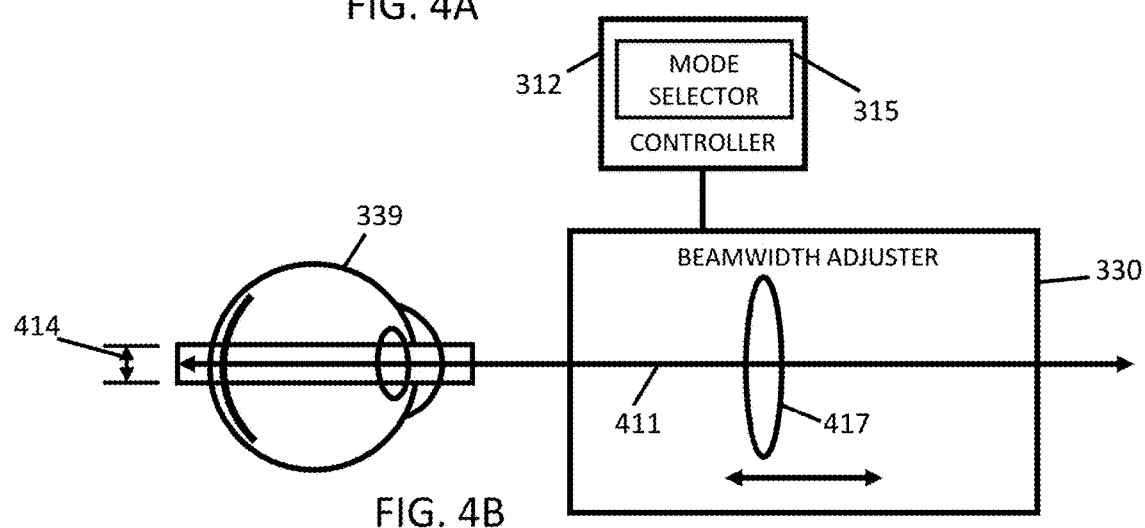
FIG. 4B is a diagram illustrating beamwidth adjustment for an example embodiment herein of an adjustable optical parameter unit.

FIG. 4B illustrates an example embodiment of beamwidth adjuster 330, and also shows eye 339 and controller 312. FIG. 4B illustrates that a beamwidth 414 can be adjusted by moving discrete lens (i.e., objective lens) 417 of beamwidth adjuster 330 along light path (i.e., sample arm) 411. In one example embodiment herein, controller 312 controls movement of lens 417 based on the mode selected by the mode selector 315, in the manner described above in connection with FIG. 3. The foregoing example is not limiting, and, in other example embodiments herein, other techniques can be employed for positioning lens 417 and adjusting the beamwidth 414.

Figure 4C:
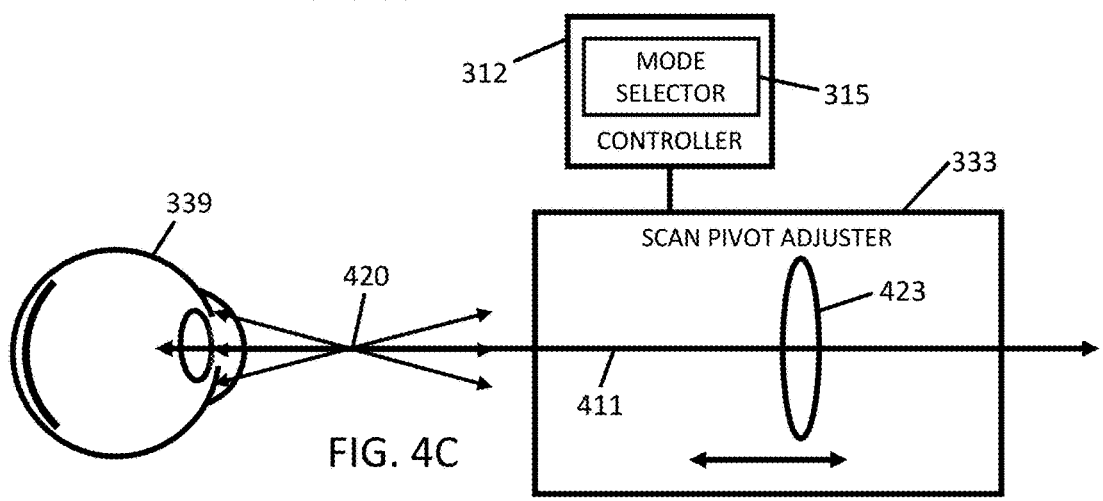
FIG. 4C is a diagram illustrating scan pivot adjustment for an example embodiment herein of an adjustable optical parameter unit.

FIG. 4C illustrates an example embodiment herein of scan pivot adjuster 333, and also shows eye 339 and controller 312. FIG. 4C illustrates that a scan pivot location 420 can be adjusted by moving discrete lens (i.e., objective lens) 423 of scan pivot adjustor 333 along light path (i.e., sample arm) 411. In one example embodiment herein, controller 312 controls the movement of lens 423 based on the mode selected by the mode selector 315, in the manner described above in connection with FIG. 3. The foregoing example is not limiting, and in other embodiments other techniques can be employed for positioning lens 423 and scan pivot location 420.

In one example embodiment herein, the lenses 408, 417, and 423 form the objective lenses described above in connection with the adjusters 328, 330, 333, respectively, of FIG. 3. In another example embodiment herein, the lenses 408, 417, 423 may be a same single lens, or another number of lenses, at least one or more of which, in some example embodiments herein, can be shared by more than one of the adjusters 328, 330, 333. Moreover, the path 411 represented in FIGS. 4A-4C may be a same optical path in the sample arm used by each or at least some of the adjusters 328, 330, 333, or one or more of the lenses (e.g., 408, 417, 423) can be provided in one or more separate paths within the sample arm. Accordingly, the examples represented in FIGS. 4A-4C are not intended to be limiting to the scope of the invention. Also, as described above, in one example embodiment herein, one or more of the focus adjuster 328 (and lens 408), beamwidth adjuster 330 (and lens 417), and scan pivot adjuster 333 (and lens 423) can include components of the Cua publication described above, and/or the lens system 800, and such components can be the same or separate from one another. In a further example embodiment herein, the mentioned components of the focus adjuster 328, beamwidth adjuster 330, and scan pivot adjuster 333 can be the same or separate, although the focus adjuster 328, beamwidth adjuster 330, and scan pivot adjuster 333 are represented separately in FIG. 3.

Figure 5:
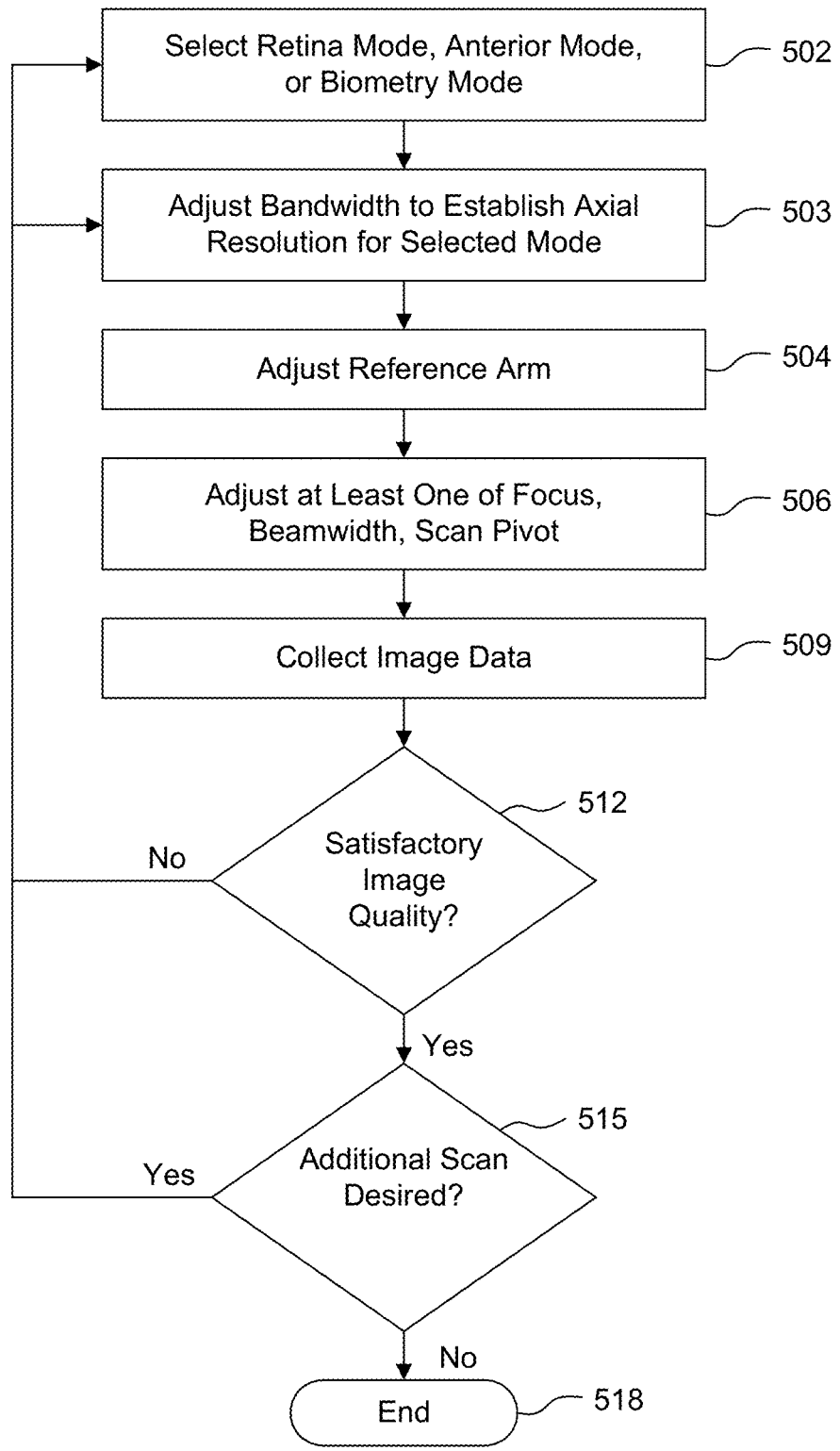
FIG. 5 is a flow diagram of a method for multimode eye analysis according to an example embodiment herein.

FIG. 5 will now be described with reference to FIGS. 1A-1F, and FIG. 3. FIG. 5 is a flow diagram of a method of multimode eye analysis according to an example embodiment herein. At step 502 mode selector 315 selects a particular one of a plurality of available eye analysis modes, such as, for example, the retina mode, anterior segment mode, or biometry mode. In one example embodiment herein, step 502 also can include selecting a sub-mode of the selected mode. By example and without limitation, selection of the sub-mode in step 502 can include selection of a diverging scan as in FIG. 1B or a telecentric scan as in FIG. 1D, in a case where the anterior segment mode is selected, or selection of a diverging scan as in FIG. 1C, a diverging scan as in FIG. 1E, or a telecentric scan as in FIG. 1F, in a case where the biometry mode is selected. Which mode (and sub-mode) is selected in step 502 can depend on, by example, applicable operating criteria, and can be made by an operator specifying the mode into mode selector 315 of controller 312 by way of interface 380, or, the selection can be made automatically by the mode selector 315.

As a result of the selected mode in step 502, control passes to step 503 where at least one bandwidth of the system 300 is selected/specified by the controller 312 in accordance with the mode selected at step 502. In one example embodiment herein, step 503 can be performed by the controller 312 controlling the light source 303 and/or the adjustable parameter unit 324 to select the at least one bandwidth. By example, in the example embodiment in which the light source 303 is controlled in step 503, the controller 312 adjusts the sweep bandwidth 309 to the first predetermined sweep bandwidth, in a case where the retina mode was selected in step 502, adjusts the sweep bandwidth 309 to the second predetermined sweep bandwidth in a case where the anterior segment mode was selected in step 502, and adjusts the sweep bandwidth 309 to the third predetermined sweep bandwidth in a case where the biometry mode was selected in step 502. Also by example, in the example embodiment in which the bandwidth (e.g., spectral range) covered by the adjustable optical parameter unit 324 is controlled in step 503, the controller 312 adjusts that bandwidth to (a) the fourth predetermined bandwidth in a case where the retina mode was selected in step 502, (b) the fifth predetermined bandwidth in a case where the anterior segment mode was selected in step 502, and (c) the sixth predetermined bandwidth in a case where the biometry mode was selected in step 502. In one example embodiment herein, the controller 312 controls both the light source 303 and the adjustable optical parameter unit 324 in the above-described manner in step 503, although in other example embodiments herein the controller 312 controls only one of the light source 303 or the adjustable parameter unit 324 in the above-described manner in step 503. Also in one example embodiment herein, the controller 312 controls the light source 303 such that its frequency (and the frequency of light emitted thereby) is maintained constant or fixed at a predetermined frequency, whether the controller 312 also adjusts the sweep bandwidth 309 and/or the bandwidth covered by the adjustable optical parameter unit 324, although in other example embodiments herein the frequency need not be fixed.

As a result of the performance of step 503, a predetermined axial resolution and image depth are established corresponding to the mode selected in step 502. For example, the first predetermined sweep bandwidth and/or fourth predetermined bandwidth establish a scan with axial resolution 172 and image depth 130 (FIG. 1A), the second predetermined sweep bandwidth and/or fifth predetermined bandwidth establish a scan with axial resolution 174 and image depth 155 (FIG. 1B), and the third predetermined sweep bandwidth and/or sixth predetermined bandwidth establish a scan with axial resolution 176 and image depth 162 (FIG. 1C). Exemplary respective sweep bandwidths, axial resolutions, and image depths are, for the retina mode, a sweep bandwidth 309 of approximately 100 nanometers which results in an axial resolution 172 of approximately 5 micrometers and an image depth 130 of approximately 5.6 millimeters; for the anterior segment mode, a sweep bandwidth 309 of approximately 70 nanometers which results in an axial resolution 174 of approximately 7.1 micrometers and an image depth 155 of approximately 8.2 millimeters; and for the biometry mode, a sweep bandwidth 309 of approximately 18 nanometers which results in an axial resolution 176 of approximately 27 micrometers and an image depth 162 of approximately 32 millimeters.

Step 504 will now be described. In step 504 the controller 312 determines and establishes a predetermined location (e.g., defining a predetermined distance or depth) within the sample 339 at which the light emitted by light source 303 is to impinge the sample 339 for imaging the sample 339. This is performed by adjusting a length of the reference arm, for example, by virtue of moving mirror 387 of delay line 327 laterally in the direction indicated by arrow 390, in correspondence with the predetermined location. By example only, in a case where the retina mode was selected in step 502, then in step 504 the controller 312 moves mirror 387 to a first position corresponding to a predetermined location within box 125 and depth 130 represented in FIG. 1A. In a case where the anterior segment mode was selected in step 502, then in step 504 the controller 312 moves mirror 387 to a second position corresponding to a predetermined location within box 150 and depth 155 represented in FIG. 1B. In a case where the biometry mode was selected in step 502, then in step 504 the controller 312 moves mirror 387 to a third position corresponding to a predetermined location within box 186 and depth 162 represented in FIG. 1C. As a result of the performance of step 504, a predetermined location within the sample 339 is established for imaging the sample 339, wherein the predetermined location corresponds to the mode selected in step 502. A focal plane can be established in a vicinity of the predetermined location to achieve better focusing, as will be described below in conjunction with step 506.

At step 506, mode selector 315 of controller 312 adjusts at least one of a focal plane, beamwidth, or scan pivot for a scan, and thus an axial resolution and image depth of the scan, depending on the mode selected in step 502. By example and without limitation, in a case where the retina mode was selected in step 502, the controller 112 effects or establishes (in step 506) focal plane 145, beamwidth 135, scan pivot location 140, axial resolution 172, and image depth 130 represented in FIG. 1A. In a case where the anterior segment mode was selected in step 502, the controller 112 effects or establishes (in step 506) focal plane 161, beamwidth 157, scan pivot location 159, axial resolution 174, and image depth 155 represented in FIG. 1B. In a case where the biometry mode was selected in step 502, the controller 112 effects or establishes (in step 506) focal plane 163, beamwidth 164, scan pivot location 166, axial resolution 176, and image depth 162 represented in FIG. 1C. For the selected mode, the controller 312 can determine/establish the focal plane in step 506 by virtue of controlling a focusing position of the discrete optical element (e.g., lens 408) of focus adjuster 328 along path 411, introducing additional optical elements into the path 411, and/or controlling relative positions of the discrete optical element, the stage 336a, and/or patient interface 336, in the manner described above in connection with FIGS. 3 and 4A. Also for the selected mode, the controller 312 can determine/establish the beamwidth in step 506 by virtue of controlling a position of the discrete optical element (e.g., lens 417) of beamwidth adjuster 330 along path 411, introducing additional optical elements into the path 411, and/or controlling relative positions of the discrete optical element, the stage 336a, and/or patient interface 336, in the manner described above in connection with FIGS. 3 and 4B. Moreover, for the selected mode, the controller 312 can determine/establish the scan pivot location in step 506 by virtue of controlling a position of the discrete optical element (e.g., lens 423) of scan pivot adjuster 333 along path 411, introducing additional optical elements into the path 411, and/or controlling relative positions of the discrete optical element, the stage 336a, and/or patient interface 336, in the manner described above in connection with FIGS. 3 and 4B. In one example embodiment herein, relationships between parameters such as focusing lens position, beamwidth, sweep bandwidth, scan pivot location, focal plane, axial resolution, and image depth, can be as defined in the Bille publication, although this example is not limiting to the scope of the invention.

Exemplary respective settings for the modes are as follows. For the retina mode, the focal plane 145 is focused at the retina 120, the beam diameter 135 at the pupil 133 is maximized to achieve optimal transverse resolution of approximately 10 to 20 micrometers, and the scan pivot location 140 is aligned to the pupil 133 (FIG. 1A). For the anterior segment mode, the focal plane 161 is focused at the anterior segment (e.g., 156), the beam diameter 157 is adjusted to provide a transverse resolution of approximately 20 to 30 micrometers (which provides extended depth of field for the full anterior segment), and the scan pivot location 159 of diverging scanning light is in front of the eye (e.g., 105) to provide sufficient field of view (FIG. 1B) (e.g., in a case where a diverging sub-mode was selected in step 502). In another example of the anterior segment mode, the scanning light beam may be telecentric (rather than diverging) as illustrated in FIG. 1D (e.g., in a case where a telecentric sub-mode was selected in step 502). For the biometry mode, the focal plane 163 is focused at a center vitreous area along a length of the eye (e.g., 105), the beam diameter 164 is adjusted to provide a transverse resolution of approximately 30 to 40 micrometers to provide an extended depth of field for a full eye length measurement (FIG. 1C). For the biometry mode, the scan pivot location 166 of diverging scanning light is, in one embodiment (FIG. 1C), in front of the pupil 133, in a case where a diverging sub-mode with such a scan pivot location was selected in step 502. In another example for the biometry mode, the scan pivot location 170 (FIG. 1E) of diverging light is behind the pupil 133, in a case where a diverging sub-mode with such a scan pivot location was selected in step 502. Also, for biometry mode, the scanning light beam can be telecentric, rather than diverging, as illustrated in FIG. 1F (see e.g., light 172), in a case where a telecentric sub-mode was selected in step 502.

At step 509 an image is captured as described above with respect to FIG. 3, using the established conditions, in particular (i) the mode (and sub-mode) selected in step 502, (ii) the bandwidth(s) specified in step 503, (iii) the predetermined location (and reference arm length) established in step 504, and (iv) the focal plane location, beamwidth, scan pivot location, axial resolution, image depth, and scan type (e.g., diverging or telecentric) established in step 506. More particularly, image data representing a scanned portion of a sample, and output by balance detector 345 as a result of the eye 339 being scanned by the sample light under the foregoing conditions (i) to (iv), is collected by controller 312 and processed to produce an image. In an example embodiment herein, to process image data into an image, the intensity of the interference wave patent impinging detector 345 is converted to an electronic signal which is digitized by detector 345. Controller 312 receives the digital data. Values of samples of the digital data correlate to a visualizable quality of the sample, such as tissue brightness. Controller 312 converts the digital data to corresponding image data. The processing results in images being provided such as those shown in, for example, FIG. 2A for retina scan mode, FIG. 2B for anterior segment scan mode, and FIG. 2C for biometry scan mode, depending on which mode was selected in step 502.

At step 512, the image data collected at step 509 is evaluated by controller 312 to determine whether it yields image quality at or above a predetermined threshold of acceptability. If the data yields image quality below the predetermined threshold, then the process returns to step 503, wherein it then proceeds in the manner as described above. By example, in this instance steps 503, 504, 506, 509, and 512 are performed again in a similar manner as described above, except that in step 503 the bandwidth(s) can be adjusted for more fine tuning thereof, in step 504 the predetermined location can be adjusted or fine-tuned according to adjustment of the reference arm, and/or in step 506 further parameter adjustments can be made/fine-tuned. By example, in such a case step 503 can include varying the sweep bandwidth of light source 303 and/or adjustable optical parameter unit 324, step 504 can include varying the predetermined location (and reference arm length), and step 506 can include varying one or more of the optical parameters, to increase the quality of images obtained in step 509. Steps 503, 504, 506, 509, and 512 can occur in one or more iterations, until acceptable image quality is attained in step 512.

At step 515, a determination is made as to whether an additional scan is desired. That determination may be made automatically, for example, by automatic programming based on predetermined operation criteria, or by operator input via user interface 380. If no further scan is desired (i.e., "No" in step 515), then controller 312 also can output the image(s) obtained in step 509 via the user interface 380 and/or store the image(s) in memory 382 and/or storage medium 107. The process then terminates at step 518. If, on the other hand, it is determined in step 515 that an additional scan is desired (i.e., "Yes" in step 515), then control passes back to step 502 where the method then proceeds again in the manner described above.

It should be noted that the order of steps represented in FIG. 5 is for purposes of illustration only, and, in other embodiments, a different order of steps can be performed. By example only, step 506 can be performed before, concurrently with, or after step 503, in various example embodiments herein, or, in other example embodiments herein, other orders of steps can be provided.

It should be noted that the examples of axial resolution, bandwidth, focal plane, scan pivot location, image depth, and scan type described above are for purposes of illustration only, and the scope of the invention is not limited thereto. Moreover, it should be noted that one or more of those types of parameters can be within a predetermined range of values. Additionally, in some example embodiments herein the controller 312 can control the light source 303 such that the sweep bandwidth 309 of light emitted thereby, and/or the bandwidth of the adjustable optical parameter unit 324, can be respective predetermined discrete bandwidth(s) for the respective, corresponding mode (selected in step 502). In other example embodiments herein, the controller 312 can control (a) the sweep bandwidth 309 emitted by light source 303 and/or the bandwidth of the adjustable optical parameter unit 324 (described above in association with step 503), the predetermined location and reference arm length (described above in association with step 504), and/or (b) the optical parameters (described above in association with step 506), such they vary continuously, or continuously over predetermined time periods, during operation of one or more of the modes. Such control, in one example embodiment herein, can be performed in the method of FIG. 5 (e.g., steps 503, 504, 506) until a determination of acceptable image quality has been made in step 512.

According to another example embodiment herein, the detectors 348 and 351 of detector 345 include respective spectrometers, wherein the spectrometer of detector 348 has a capability of detecting light within a first wavelength range (corresponding to an "axial zoom in"), and the spectrometer of the detector 351 has a capability of detecting light within a second, smaller wavelength range (corresponding to an "axial zoom out"). In still another example embodiment herein, the detector 354 includes more than the two detectors 348 and 351. By example and without limitation, in one example embodiment herein the detector 345 comprises three detectors, each including a corresponding spectrometer, wherein the spectrometer of a first one of the three detectors has a capability of detecting light within the above-mentioned fourth predetermined bandwidth (e.g., spectral range), a second one of the three detectors has a capability of detecting light within the above-mentioned fifth predetermined bandwidth (e.g., spectral range), and a third one of the three detectors has a capability of detecting light within the above-mentioned sixth predetermined bandwidth (e.g., spectral range).

By virtue of the foregoing example embodiment, a predetermined axial resolution and image depth are established. For example, the fourth predetermined bandwidth effects or establishes a scan with axial resolution 172 and image depth 130 (FIG. 1A) (e.g., a first axial zoom), the fifth predetermined bandwidth effects or establishes a scan with axial resolution 174 and image depth 155 (FIG. 1B) (e.g., a second axial zoom), and the sixth predetermined bandwidth effects or establishes a scan with axial resolution 176 and image depth 162 (FIG. 1C) (e.g., a third axial zoom). In one example embodiment herein, the detector 345 having such a capability can be used in conjunction with the controlling of the sweep bandwidth 309 of the light source 303 and/or the bandwidth covered by the adjustable optical parameter unit 324, to enable the mentioned axial resolution(s) and image depth(s) to be effected or established, although in other example embodiments herein the axial resolution(s) and image depth(s) can be established using only the detector 345 without controlling the sweep bandwidth and/or the bandwidth covered by adjustable optical parameter unit 324. Also, the method of FIG. 5 can be performed using the detector 345 of the present example embodiment. For example, the steps of the method of FIG. 5 are performed in the same manner as described above, except that the controlling of one or more of the bandwidth(s) described above in association with step 503 need not be performed.

A further example aspect herein will now be described. According to this example aspect, an auto-referencing technique is provided that can be performed in a manner that substantially minimizes or avoids use of iterative steps and procedures to perform auto-referencing according to conventional techniques. In one example embodiment herein, auto-referencing is performed in single instance (or series of steps) or in a manner that substantially reduces or avoids the iterative nature of conventional techniques.

In accordance with an example embodiment herein, auto-referencing is enabled by virtue of controlling an imaging depth, such as, by example and without limitation, by way of controlling at least one bandwidth of the system 300. According to one example embodiment herein, such controlling includes the controller 312 controlling a wavelength sweep amplitude (e.g., 309) of a swept source laser (e.g., light source 303), and/or controlling at least one bandwidth covered by the system 300. In the case of the wavelength sweep amplitude, in one example embodiment herein, a detection sampling rate is maintained constant while a wavelength sweep range is reduced, and, as a result, the imaging depth increases accordingly even though in some examples axial resolution may be compromised. In one example, this assumes that an instantaneous linewidth of the swept source laser is not a limiting factor for sampling. In one example embodiment herein, light source 303 includes a vertical cavity surface emitting laser (VCSEL). A VCSEL can narrow an instantaneous linewidth, resulting in several hundreds of millimeters in coherence length. As such, imaging depth can be increased to several tens of millimeters in cases where, for example, the detection bandwidth is not limited.

Figure 7:
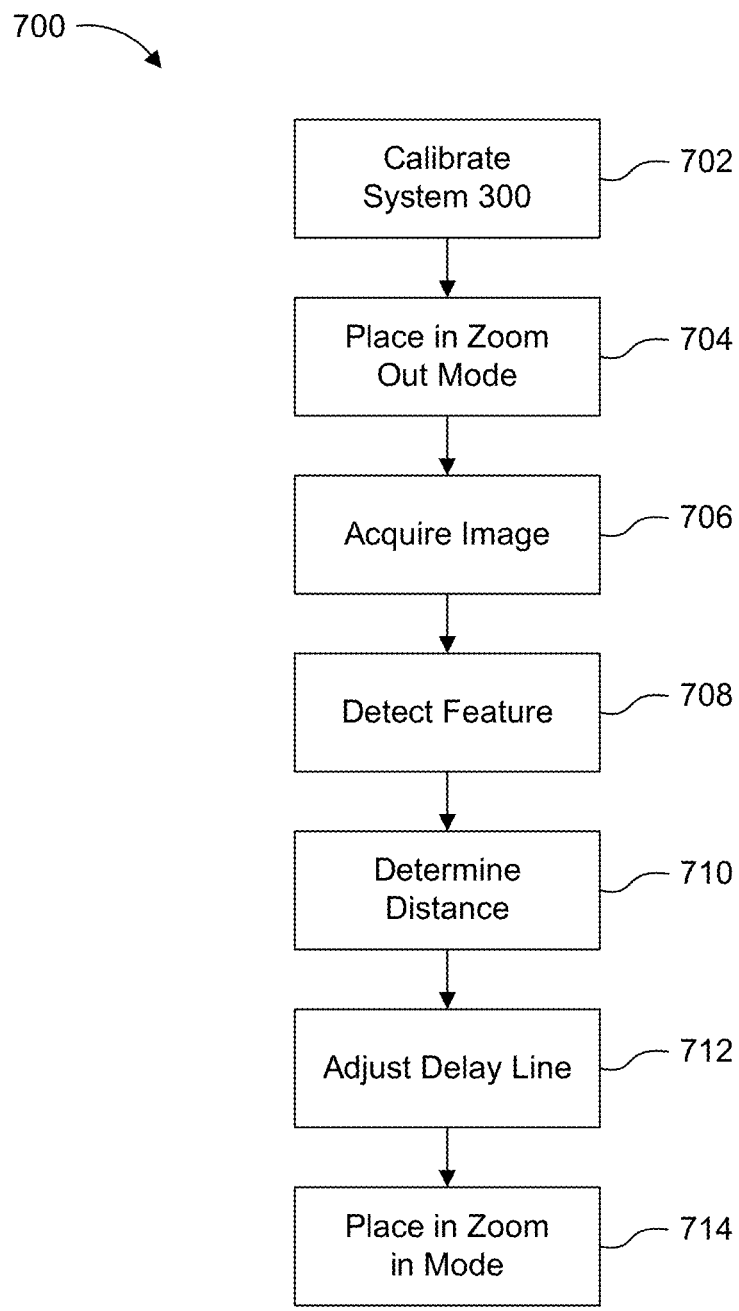
FIG. 7 is a flow diagram of a method for performing auto-referencing according to an example embodiment herein.

Reference is now made to FIG. 7, which depicts a flow diagram of a method 700 for performing auto-referencing, according to an example embodiment herein. In one example embodiment herein, the method 700 is performed as part of method shown in FIG. 5. By example and without limitation, the method 700 can be performed either as a separate step within the method of FIG. 5, or as part of one of the steps shown in FIG. 5, such as, without limitation, step 503, 504, and/or 506. In still other example embodiments herein, the method 700 can be performed as a standalone method, or during patient alignment.

The below description of the method 700 is described in the context of the method being performed after step 502 of FIG. 5, and prior to step 503 of FIG. 5, although that example is not limiting to the scope of the invention. As described above, step 502 includes the selecting of one of the plurality of available operating modes, by mode selector 315.

Thereafter, step 702 is performed. Step 702 involves calibrating the system 300 by determining a nominal initial location or setting of the optical delay line 327. In one example embodiment herein, the determining of the nominal location of the delay line 327 is performed based on predetermined characteristics of a predetermined sample (e.g., eye) model. One example of a predetermined sample model and characteristics that can be employed is disclosed in a publication by Rafael Navarro entitled "The Optical Design of the Human Eye: a Critical Review", Journal of Optometry, Volume 2, Issue 1, pages 3-18 (2009), which is incorporated by reference herein in its entirety as if set forth fully herein. In other example embodiments herein, other sample models can be employed instead. In one example embodiment herein, the determining of the nominal location in step 702 is performed as follows. In particular, the controller 312 determines and establishes a predetermined (imaginary) location (e.g., defining a predetermined distance or depth) within the sample model at which light to be emitted by light source 303 is to impinge the predetermined sample model, for a hypothetical imaging of the predetermined sample model. This is performed by adjusting a length of the reference arm, for example, by virtue of moving mirror 387 of delay line 327 laterally in the direction indicated by arrow 390, in correspondence with the predetermined (imaginary) location. In one example embodiment herein, the length of the reference arm is adjusted in step 702 by adjusting the optical delay line 327 such that a predetermined feature, such as a retina feature of the predetermined sample model in a case where the retina mode was selected in step 502, an anterior segment feature of the predetermined sample model in a case where the anterior segment mode was selected in step 502, or a biometry feature of the predetermined sample model in a case where the biometry mode was selected in step 502, is deemed to be within an axial imaging range of the OCT imaging system 300, in which case the delay line 327 is deemed placed in the nominal location.

By example only, in a case where the retina mode was selected in step 502, then in step 702 the controller 312 moves mirror 387 to a vicinity of a first position corresponding to a predetermined location within box 125 and depth 130 represented in FIG. 1A. In a case where the anterior segment mode was selected in step 502, then in step 702 the controller 312 moves mirror 387 to a vicinity of a second position corresponding to a predetermined location within box 150 and depth 155 represented in FIG. 1B. In a case where the biometry mode was selected in step 502, then in step 702 the controller 312 moves mirror 387 to a vicinity of a third position corresponding to a predetermined location within box 186 and depth 162 represented in FIG. 1C. As a result of the performance of step 702, the nominal location of the delay line 327 is set based on the predetermined characteristics of the predetermined sample (e.g., eye) model and the mode selected in step 502.

A next step 704 includes controlling the system 300 to reduce its axial resolution and increase its imaging depth to a first predetermined axial resolution and imaging depth, thereby placing the system 300 in a selected one of a plurality of available zoom modes, such as, by example and without limitation, a "zoom out" mode. In one example embodiment herein, step 704 can be performed by the controller 312 controlling the light source 303 and/or the adjustable optical parameter unit 324 to select at least one bandwidth that causes the system 300 to be placed in the "zoom out" mode (e.g., FIG. 1b or FIG. 1c). In an example embodiment where the light source 303 is controlled in step 702, the controller 312 adjusts the sweep bandwidth 309 to a selected sweep bandwidth from among a plurality of available sweep bandwidths such as the first, second, and/or third predetermined sweep bandwidths, wherein the selected sweep bandwidth corresponds to the "zoom out" mode. In one example embodiment herein the selected sweep bandwidth is within a first narrow predetermined sweep bandwidth range that causes the system 300 to have a corresponding predetermined axial resolution and imaging depth. Also, in an example embodiment where the adjustable optical parameter unit 324 is controlled in step 704, the controller 312 adjusts the bandwidth covered by the adjustable optical parameter unit 324 (e.g., by way of focus adjuster 328), such that it covers a selected bandwidth from among a further plurality of available bandwidths such as the fourth predetermined bandwidth, fifth predetermined bandwidth, and/or sixth predetermined bandwidth, wherein the selected bandwidth corresponds to the "zoom out" mode. By example and without limitation, the selected bandwidth in that example embodiment is a spectral bandwidth range that provides the first predetermined axial resolution and imaging depth.

In an example embodiment herein, the controller 312 controls only the light source 303 or adjustable parameter unit 324 in the above-described manner to provide the first predetermined axial resolution and imaging depth. However, in other example embodiments herein the controller 312 controls both the light source 303 and adjustable parameter unit 324 such that, together, they provide the first predetermined axial resolution and imaging depth. Also, in one example embodiment herein, the first narrow predetermined sweep bandwidth range and/or the spectral bandwidth range is 20 nm, the first predetermined axial resolution is 24 micrometers, and the first imaging depth is a long imaging depth of 28 mm.

It should be noted that, although the foregoing example embodiments are described in the context of there being three predetermined sweep bandwidths available for selection of sweep bandwidth 309 in step 704, and three predetermined bandwidths available for selection in the adjustable optical parameter unit 324 in step 704, these examples are not limiting, and, in other example embodiments herein, there may be more of less than those numbers of available bandwidths.

Step 706 will now be described. In step 706, an image is taken of a predetermined part or location of an actual subject, such as, e.g., sample (e.g., eye) 339. This step 706 can include, in one example embodiment herein, the system 300 being operated to take a B-scan of a predetermined part of a retina, using the modes set in steps 502 and 704. In one example embodiment herein, step 706 can be performed in a similar manner as step 509 of FIG. 5 described above, but based on the mode (and sub-mode) selected in step 502 and the "zoom out" mode established in step 704.

In one example embodiment herein, in step 706 OCT measurements can be acquired that show positions of structures of the sample 339 relative to an expected position of a pivot plane. For example, a B-scan, or two-dimensional tomogram, can be obtained in step 706 by scanning the sample beam linearly across a predetermined feature or location (e.g., the retina, anterior segment, or biometry features, depending on which mode was selected in step 502) of the sample 339 while obtaining A-scans, which are axial reflectivity depth profiles obtained as Fourier transforms of an interferogram acquired by the detector 345.

According to an example embodiment herein, the system 300 can obtain both A-scans and B-scans, although in other embodiments herein the scans can be obtained using more than one respective system 300, i.e., one system for obtaining A-scans and another system for obtaining B-scans.

In step 708 a position and/or location of the predetermined feature or location of the sample 339 within the imaging depth, is determined using, according to an example embodiment herein, a predetermined algorithm. In one example embodiment herein, the predetermined algorithm is an edge detection algorithm and/or a feature detection algorithm that detects/determines boundaries and/or positions of the predetermined feature or location, although in other example embodiments herein, other types of algorithms can be employed.

In step 710 a determination is made of a distance between the position and/or location determined in step 708 and a predetermined part of the B-scan, such as, by example, a top part or upper part of the B-scan. In one example embodiment herein, the determination is made based on a measurement or estimation of a number of pixels included in the image from the position and/or location determined in step 708 to the predetermined part of the B-scan, or vice versa, given that the number of pixels in the image, and pixel sizes in physical dimensions, are pre-known.

In step 712, the optical delay line 327 is adjusted based on the distance determined in step 710. By example and without limitation, the optical delay line 327 is adjusted by displacing the mirror 387 along the optical delay line 327 by, or based on, the distance determined in step 710. As such, the delay line 327 is adjusted to cause the specific axial location at which the sample 339 is scanned to include the predetermined feature or location.

Step 714 includes controlling the system 300 to change its axial resolution and imaging depth, to thereby place the system 300 in another selected one of a plurality of available zoom modes, such as, by example and without limitation, a "zoom in" mode (e.g., FIG. 1a or FIG. 1b). In one example embodiment herein, step 714 is performed by the controller 312 controlling the light source 303 to select another predetermined sweep bandwidth from among the plurality of available sweep predetermined bandwidths. By example and without limitation, in step 714 the controller 312 controls the light source 303 such that its sweep bandwidth is within a second, wider predetermined sweep bandwidth range that causes the system 300 to have a further predetermined axial resolution and a further imaging depth.

Also, in an example embodiment in which the adjustable parameter unit 324's bandwidth is controlled in step 714, the controller 312 adjusts the bandwidth covered by the adjustable parameter unit 324 (e.g., by way of focus adjuster 328), such that it covers a selected one of the predetermined bandwidths (e.g., from among the fourth predetermined bandwidth, fifth predetermined bandwidth, and sixth predetermined bandwidth), wherein the selected bandwidth corresponds to the "zoom out" mode. By example and without limitation, the selected bandwidth is a spectral bandwidth range that provides or corresponds to the further predetermined axial resolution and the further imaging depth.

In an example embodiment herein, in step 714 the controller 312 controls only the light source 303 or adjustable parameter unit 324 in the above-described manner in step 714 to provide the further predetermined axial resolution and further imaging depth. However, in other example embodiments herein the controller 312 controls both the light source 303 and adjustable optical parameter unit 324 in step 714 such that, together, they provide the further predetermined axial resolution and further imaging depth. By example and without limitation, in either of the embodiments, the second, wider predetermined sweep bandwidth range and/or the further spectral bandwidth range is 100 nm, the further predetermined axial resolution is 4.8 micrometers, and the further imaging depth is 5.6 mm.

As a result of the performance of steps 702 to 714, the system 300 is deemed to be set in a state in which it is ready to capture an image of the sample 339, such as, by example, a retina, anterior segment, or biometry feature of the eye, depending on the mode selected in step 502. In one example embodiment herein, after step 714 is performed, the method of FIG. 5 can be returned to. By example, after step 714 is performed, control can pass back to step 503, 504, 506, or 509, although this example is not exclusive. In other example embodiment herein, the method 700 ends after step 714 is performed, or control passes back to step 702 where the method 700 can be performed again, depending on applicable operating criteria.

By virtue of the method 700 of FIG. 7, iterative processes used in conventional auto-referencing techniques are substantially reduced or avoided. In one example embodiment herein, the method of FIG. 7 can be completed automatically within 100 to 200 microseconds, which is an order of magnitude less reduction in execution time relative to those of conventional auto-referencing processes. As such, the method of FIG. 7 substantially reduces the possibility of image degradation caused by patient movements, as often is the case with conventional iterative auto-reference techniques. The method of FIG. 7 is therefore more efficient and better performing than the conventional techniques.

It should be noted that, in other example embodiments herein, step 704 and/or 714 can be performed to provide different "zoom" states than those described above, and, in other example embodiments herein, step 704 and/or 714 need not be performed at all, depending on applicable operating criteria. Also, although step 714 is described in the context of providing a "zoom out" mode, in other example embodiments herein, step 714 can be performed to provide other zoom states that are deemed appropriate for acquiring applicable images.

According to another example embodiment herein in which the detector 345 includes a plurality of the detectors, as described above, each of the detectors can comprise a respective spectrometer. In the example embodiment described hereinabove wherein the detector 345 includes three detectors, the spectrometer of a first one of the three detectors has a capability of detecting light within the above-mentioned fourth predetermined bandwidth (e.g., spectral range), a second one of the three detectors has a capability of detecting light within the above-mentioned fifth predetermined bandwidth (e.g., spectral range), and a third one of the three detectors has a capability of detecting light within the above-mentioned sixth predetermined bandwidth (e.g., spectral range).

By virtue of the foregoing example embodiment, the first and further axial resolutions and the predetermined image depths can be established. For example, the fourth predetermined bandwidth establishes a scan with axial resolution 172 and image depth 130 (FIG. 1A), the fifth predetermined bandwidth establishes a scan with axial resolution 174 and image depth 155 (FIG. 1B), and the sixth predetermined bandwidth establishes a scan with axial resolution 176 and image depth 162 (FIG. 1C). In one example embodiment herein, the detector 345 having the plurality of spectrometers can be used in conjunction with the controlling of the sweep bandwidth of the light source 303 and/or the bandwidth covered by the optical parameter unit 324, to establish the axial resolution(s) and image depth(s), although in other example embodiments the axial resolution(s) and image depth(s) can be established using only the detector 345 but not by virtue of controlling the sweep bandwidth and bandwidth covered by the optical parameter unit 324. As such, in that example embodiment herein steps 704 and 714 do not include the controlling of those bandwidth(s).

In view of the foregoing disclosure, a multimode eye analysis system, method, and computer readable medium according to example aspects herein are provided that enable a plurality of types of eye analysis to be provided by a single evaluation device/system, substantially without compromising on imaging quality and while substantially minimizing (or not requiring) use of separate mode components. By virtue thereof, the system can be adaptably and dynamically tuned to provide superior image analysis for each of the plurality of eye analysis types, including, for example, at least retina imaging, anterior segment imaging, biometry imaging, and other diagnostics as well. Moreover, the system, method and computer readable medium herein do not require a long delay line adjustment as typically required in conventional systems (e.g., including conventional systems requiring multiple delay line adjustments and multiple image capture), nor do the system, method and computer readable medium herein require high precision along the delay line. While conventional systems may attempt to measure along a Z-axis by moving a delay line or varying a light source frequency, the example aspects herein, on the other hand, operate instead based on an adjustment of at least one bandwidth of the system 300 (and thus adjustment of imaging depth and axial resolution), as described hereinabove. Conventional systems particularly also do not operate in such a manner with respect to one or more various modes, including, without limitation, a mode in a biometry domain. [

Also, use of a swept source laser (e.g., laser 303*a*) according to example embodiments herein enables changing of a wavelength sweep amplitude of light for scanning a sample (e.g., sample 339), and thereby enables adjustment of imaging depths that are attained during scanning by virtue of the method(s), system(s), and computer-readable media herein. In one example embodiment herein, a sampling rate of the swept source laser is constant. As a result, when the wavelength sweep range is reduced, imaging depth can increase, even if it happens that axial resolution becomes compromised (or not compromised). As explained above, in one example embodiment herein, light source 303 includes a vertical cavity surface emitting laser (VCSEL). A VCSEL can narrow an instantaneous linewidth, resulting in several hundreds of millimeter coherence length. As such, imaging depth can be increased to several tens of millimeters in cases where, for example, the detection bandwidth is not limited. Moreover, according to one example embodiment herein, different axial resolutions and image depths can be selected by the controller 312 for different eye analysis modes, by controlling the sweep bandwidth 309. By example only, the controller 312 can control the sweep bandwidth 309 such that its width is set to a width that corresponds to a selected one of the eye analysis modes, to thereby provide the selected axial resolution and image depth, even though, according to one example embodiment herein, the frequency of the light source 303 (and light emitted thereby) is maintained fixed or constant at a predetermined frequency. In that example embodiment, the selected axial resolution and image depth are provided without adjusting the frequency of the light source 303 (and light emitted thereby).

Moreover, although the samples 105 and 339 are described as being at least part(s) of a human eye, in other example embodiments they may be other types of samples, such as a non-human eye, or other sample types.

In the foregoing description, example aspects are described with reference to several example embodiments. Accordingly, the specification should be regarded as illustrative, rather than restrictive. Similarly, the figures illustrated in the drawings, which highlight the functionality and advantages of the example embodiments, are presented for example purposes only. The architecture of the example embodiments is sufficiently flexible and configurable, such that it may be utilized (and navigated) in ways other than those shown in the accompanying figures.

Software embodiments of the examples presented herein may be provided as a computer program, or software, such as one or more programs having instructions or sequences of instructions, included or stored in an article of manufacture such as a machine-accessible or machine-readable medium, an instruction store, computer-readable storage medium or computer-readable storage device, each of which can be non-transitory, in one example embodiment. The program or instructions on the non-transitory machine-accessible medium, machine-readable medium, instruction store, computer-readable storage medium, or computer-readable storage device, may be used to program a computer system or other electronic device. The machine- or computer-readable medium, instruction store, and storage device may include, but are not limited to, floppy diskettes, optical disks, and magneto-optical disks or other types of media/machine-readable medium/instruction store/storage device suitable for storing or transmitting electronic instructions. The techniques described herein are not limited to any particular software configuration. They may find applicability in any computing or processing environment. The terms "computer-readable", "machine-accessible medium", "machine-readable medium", "instruction store", and "computer-readable storage device" used herein shall include any medium that is capable of storing, encoding, or transmitting instructions or a sequence of instructions for execution by the machine, computer, or computer processor and that causes the machine/computer/computer processor to perform any one of the methods described herein. Furthermore, it is common in the art to speak of software, in one form or another (e.g., program, procedure, process, application, module, unit, logic, and so on), as taking an action or causing a result. Such expressions are merely a shorthand way of stating that the execution of the software by a processing system causes the processor to perform an action to produce a result.

Some embodiments may also be implemented by the preparation of application-specific integrated circuits, field-programmable gate arrays, or by interconnecting an appropriate network of conventional component circuits.

Some embodiments include a computer program product. The computer program product may be a storage medium or media, instruction store(s), or storage device(s), having instructions stored thereon or therein which can be used to control, or cause, a computer or computer processor to perform any of the procedures of the example embodiments described herein. The storage medium/instruction store/storage device may include, by example and without limitation, an optical disc, a ROM, a RAM, an EPROM, an EEPROM, a DRAM, a VRAM, a flash memory, a flash card, a magnetic card, an optical card, nanosystems, a molecular memory integrated circuit, a RAID, remote data storage/ archive/warehousing, and/or any other type of device suitable for storing instructions and/or data.

Stored on any one of the computer-readable medium or media, instruction store(s), or storage device(s), some implementations include software for controlling both the hardware of the system and for enabling the system or microprocessor to interact with a human user or other mechanism utilizing the results of the example embodiments described herein. Such software may include without limitation device drivers, operating systems, and user applications. Ultimately, such computer-readable media or storage device(s) further include software for performing example aspects of the invention, as described above.

Included in the programming and/or software of the system are software modules for implementing the procedures described herein. In some example embodiments herein, a module includes software, although in other example embodiments herein, a module includes hardware, or a combination of hardware and software.

While various example embodiments of the present invention have been described above, it should be understood that they have been presented by way of example, and not limitation. It will be apparent to persons skilled in the relevant art(s) that various changes in form and detail can be made therein. Thus, the present invention should not be limited by any of the above described example embodiments, but should be defined only in accordance with the following claims and their equivalents.

Further, the purpose of the Abstract is to enable the Patent Office and the public generally, and especially the scientists, engineers and practitioners in the art who are not familiar with patent or legal terms or phraseology, to determine quickly from a cursory inspection the nature and essence of the technical disclosure of the application. The Abstract is not intended to be limiting as to the scope of the example embodiments presented herein in any way. It is also to be understood that the procedures recited in the claims need not be performed in the order presented.

While this specification contains many specific embodiment details, these should not be construed as limitations on the scope of any inventions or of what may be claimed, but rather as descriptions of features specific to particular embodiments described herein. Certain features that are described in this specification in the context of separate embodiments can also be implemented in combination in a single embodiment. Conversely, various features that are described in the context of a single embodiment can also be implemented in multiple embodiments separately or in any suitable sub-combination. Moreover, although features may be described above as acting in certain combinations and even initially claimed as such, one or more features from a claimed combination can in some cases be excised from the combination, and the claimed combination may be directed to a sub-combination or variation of a sub-combination.

In certain circumstances, multitasking and parallel processing may be advantageous. Moreover, the separation of various components in the embodiments described above should not be understood as requiring such separation in all embodiments, and it should be understood that the described program components and systems can generally be integrated together in a single software product or packaged into multiple software products.

Having now described some illustrative embodiments and embodiments, it is apparent that the foregoing is illustrative and not limiting, having been presented by way of example. In particular, although many of the examples presented herein involve specific combinations of apparatus or software elements, those elements may be combined in other ways to accomplish the same objectives. Acts, elements and features discussed only in connection with one embodiment are not intended to be excluded from a similar role in other embodiments or embodiments.

The apparatus and computer programs described herein may be embodied in other specific forms without departing from the characteristics thereof. The foregoing embodiments are illustrative rather than limiting of the described systems and methods. Scope of the apparatus and computer programs described herein is thus indicated by the appended claims, rather than the foregoing description, and changes that come within the meaning and range of equivalency of the claims are embraced therein.

What is claimed is:

1. A multimode optical coherence tomography (OCT) imaging system comprising:
   a light source arranged to emit coherence light in a path to scan a sample;
   an optical parameter unit through which the coherence light propagates in the path;
   a detector arranged to detect reflected light, the reflected light being light reflected in the path as a result of the coherence light scanning the sample by way of the optical parameter unit; and
   a controller arranged to control at least one of the light source or the optical parameter unit, the controller performing a set of operations comprising:
      receiving an indication of a selected mode from a plurality of available operating modes of the multimode OCT system, the plurality of available operating modes including at least a first mode, a second mode and a third mode, wherein each of the plurality of available operating modes:
         has an associated scan pivot location relative to the sample;
         has a different corresponding bandwidth than other operating modes of the plurality of available operating modes; and
         provides at least one of a corresponding predetermined axial resolution or a corresponding predetermined imaging depth; and
      configuring at least one of a bandwidth or a scan pivot location of the multimode OCT system based on the selected operating mode.

2. The system of claim 1, wherein the detector comprises a plurality of spectrometers, and each spectrometer detects reflected light within a respective spectral range corresponding to a respective one of the plurality of available operating modes.

3. The system of claim 1, wherein the light source comprises a swept source laser and controller controls the light source by controlling a sweep bandwidth of the swept source laser.

4. The system of claim 1, wherein the light source comprises a super-luminescent diode.

5. The system of claim 1, wherein the controller controls the optical parameter unit by controlling a bandwidth thereof, to thereby control a spectral bandwidth over which reflected light is detected by the detector.

6. The system of claim 5, wherein at least one of the bandwidth or the spectral bandwidth corresponds to the at least one selected mode.

7. The system of claim 1, wherein the first mode is a retina mode, the second mode is an anterior segment mode, and the third mode is a biometry mode.

8. The system of claim 7, wherein the corresponding predetermined axial resolution provided by the retina mode is higher than the corresponding predetermined axial resolution provided by the anterior segment mode, and the corresponding predetermined axial resolution provided by the anterior segment mode is higher than the corresponding predetermined axial resolution provided by the biometry mode.

9. The system of claim 7, wherein the controller is coupled to the detector and obtains an image of the sample based on the reflected light, the image includes a retina image in a case where the at least one selected mode is the retina mode, an anterior segment image in a case where the at least one selected mode is the anterior segment mode, and a biometry image in a case where the at least one selected mode is the biometry mode.

10. The system of claim 1, wherein the controller controls the optical parameter unit to establish at least one of a predetermined focal plane, a predetermined bandwidth, or a scan pivot location, corresponding to the at least selected mode.

11. The system of claim 1, wherein the optical parameter unit comprises a discrete optical element movable along the path.

12. The system of claim 1, wherein the path is a sample path of the multimode OCT imaging system, the multimode OCT imaging system also comprises a reference path, and the controller is coupled to the detector and obtains an image of the sample based on the reflected light.

13. The system of claim 12, wherein the controller also is arranged to perform auto-referencing, the auto-referencing including:
    detecting a distance between a predetermined feature in the image and another predetermined part of the image; and
    adjusting a length of the reference path based on the distance.

14. The system of claim 13, wherein the auto-referencing further includes:
    prior to the detecting of the distance, placing the multimode OCT imaging system in a first zoom mode; and
    after the adjusting, placing the multimode OCT imaging system in a second zoom mode, wherein the first zoom mode is a zoom out mode and the second zoom mode is a zoom in mode.

15. The system of claim 1, wherein each associated scan pivot location is in front of, or within, the sample.

16. The system of claim 1, wherein the coherence light scans the sample in a diverging or telecentric manner.

17. The system of claim 1, wherein the light source emits the coherence light at a frequency that is constant.

18. A method for operating a multimode optical coherence tomography (OCT) imaging system, comprising:
    selecting at least one mode from among a plurality of available operating modes of the multimode OCT imaging system, the plurality of available operating modes including at least a first mode, a second mode, and a third mode;
    operating a light source to emit coherence light in a path towards a sample; and
    operating an optical parameter unit, arranged in the path between the light source and the sample, to configure at least one of a bandwidth or a scan pivot location of the multimode OCT imaging system in accordance with the selected at least one mode,
    wherein each of the plurality of available operating modes:
        has an associated scan pivot location relative to the sample;
        has a different corresponding bandwidth than other operating modes of the plurality of available operating modes; and
        provides at least one of a corresponding predetermined axial resolution or a corresponding predetermined imaging depth.

19. The method of claim 18, wherein the first mode is a retina mode, the second mode is an anterior segment mode, and the third mode is a biometry mode.

20. The method of claim 19, wherein the corresponding predetermined axial resolution provided by the retina mode is higher than the corresponding predetermined axial resolution provided by the anterior segment mode, and the corresponding predetermined axial resolution provided by the anterior segment mode is higher than the corresponding predetermined axial resolution provided by the biometry mode.

21. The method of claim 18, further comprising detecting reflected light by way of a detector, the reflected light being light reflected in the path as a result of the coherence light scanning the sample.

22. The method of claim 21, wherein the detector comprises a plurality of spectrometers, and, in the detecting, each spectrometer detects reflected light within a respective spectral range corresponding to a respective one of the plurality of available operating modes.

23. The method of claim 21, wherein the operating of the optical parameter unit includes controlling a bandwidth of the optical parameter unit in accordance with the selected at least one mode, to thereby control a spectral bandwidth over which reflected light is detected by the detector.

24. The method of claim 18, further comprising controlling at least one of the light source or the optical parameter unit in accordance with the selected at least one mode.

25. The method of claim 18, wherein the light source comprises a swept source laser and the operating of the light source includes controlling a sweep bandwidth of the swept source laser in accordance with the selected at least one mode.

26. The method of claim 18, wherein the path is a sample path of the multimode OCT imaging system, the multimode OCT imaging system also comprises a reference path, and the method further comprises obtaining an image of the sample based on the reflected light.

27. The method of claim 26, further comprising performing auto-referencing, the auto-referencing including:
    detecting a distance between a predetermined feature in the image and another predetermined part of the image; and
    adjusting a length of the reference path based on the distance.

28. The method of claim 27, wherein the auto-referencing further includes:
    prior to the detecting of the distance, placing the multimode OCT imaging system in a first zoom mode; and
    after the adjusting, placing the multimode OCT imaging system in a second zoom mode, wherein the first zoom mode is a zoom out mode and the second zoom mode is a zoom in mode.

29. The method of claim 18, wherein selecting the at least one mode comprises receiving user input comprising a selection of the at least one mode from the plurality of available operating modes.

30. A non-transitory computer readable medium storing a program that, when executed by a computer processor, causes the computer processor to perform a method for operating a multimode Optical Coherence Tomography (OCT) imaging system, the method comprising:

selecting at least one mode from among a plurality of available operating modes of the multimode OCT imaging system, the plurality of available operating modes including at least a first mode, a second mode, and a third mode;

operating a light source to emit coherence light in a path towards a sample; and operating an optical parameter unit, arranged in the path between the light source and the sample, to configure at least one of a bandwidth or a scan pivot location of the multimode OCT imaging system in accordance with the selected at least one mode, wherein each of the plurality of available operating modes:
has an associated scan pivot location relative to the sample;
has a different corresponding bandwidth than the other operating modes of the plurality of available operating modes; and
provides at least one of a corresponding predetermined axial resolution or a corresponding predetermined imaging depth.

31. The non-transitory computer readable medium of claim 30, wherein the first mode is a retina mode, the second mode is an anterior segment mode, and the third mode is a biometry mode.

* * * * *